US012752014B2

(12) United States Patent
Paulson et al.

(10) Patent No.: US 12,752,014 B2
(45) Date of Patent: Oct. 6, 2026

(54) DISRUPTION OF CD28-SIALOSIDE LIGAND COMPLEXES TO ENHANCE T CELL ACTIVATION

(71) Applicant: THE SCRIPPS RESEARCH INSTITUTE, La Jolla, CA (US)

(72) Inventors: James C. Paulson, Del Mar, CA (US); Landon J. Edgar, San Diego, CA (US); Andrew J. Thompson, San Diego, CA (US); Chika Kikuchi, San Diego, CA (US); Brett Garabedian, Del Mar, CA (US); Xiaoshuang Wang, San Diego, CA (US); Eleanor Bashian, Laguna Niguel, CA (US)

(73) Assignee: The Scripps Research Institute, La Jolla, CA (US)

( * ) Notice: Subject to any disclaimer, the term of this patent is extended or adjusted under 35 U.S.C. 154(b) by 730 days.

(21) Appl. No.: 18/041,715

(22) PCT Filed: Jul. 21, 2021

(86) PCT No.: PCT/US2021/042577

§ 371 (c)(1),
(2) Date: Feb. 15, 2023

(87) PCT Pub. No.: WO2022/020473

PCT Pub. Date: Jan. 27, 2022

(65) Prior Publication Data

US 2023/0293711 A1 Sep. 21, 2023

Related U.S. Application Data

(60) Provisional application No. 63/054,516, filed on Jul. 21, 2020.

(51) Int. Cl.

| | |
|---|---|
| ***A61K 47/68*** | (2017.01) |
| ***C07K 16/28*** | (2006.01) |
| ***C12N 9/24*** | (2006.01) |

(52) U.S. Cl.

CPC ...... *A61K 47/6815* (2017.08); *A61K 47/6849* (2017.08); *C07K 16/2818* (2013.01); *C07K 16/2896* (2013.01); *C12N 9/2402* (2013.01); *C12Y 302/01018* (2013.01)

(58) Field of Classification Search

None
See application file for complete search history.

(56) References Cited

U.S. PATENT DOCUMENTS

2014/0234296 A1* 8/2014 Sharma ................ A61K 9/0019 424/133.1
2019/0248919 A1* 8/2019 Woods ........... C12Y 302/01018
2022/0372458 A1* 11/2022 Peng .................. A61K 47/6815

* cited by examiner

*Primary Examiner* — Celeste A Roney

(74) *Attorney, Agent, or Firm* — Hugh Wang; Thomas Fitting

(57) ABSTRACT

The present invention provides methods for enhancing T cell activation and expansion, and methods for stimulating a T cell immune response in a subject. The methods of the invention involve the use of a targeting agent-enzyme conjugate that contains (a) a targeting moiety that specifically binds a cell surface molecule on T cells, and (b) a sialidase or enzymatically active fragment thereof. Also provided in the invention are targeting agent-enzyme conjugates that can be used in the therapeutic methods, including antibody conjugates that are formed of a sialidase and a T cell targeting antibody (e.g., an anti-PD1 antibody).

20 Claims, 12 Drawing Sheets

```
        PD-1 (57) DKLAAF--PEDRS-QPGQDCRFRVTQLP-NGRDFHMSVVRARRNDSGTYLCGAISLAPKAQIK
       PD-L1 (57) --FVHGE-EDLKVQHSSYRQRARLLKDQLSLGNAALQITDVKLQDAGVYRCMISYGGA-DYKR
       PD-L2 (58) -------------DT-SPHRERATLLEEQLPLGKASFHIPQVQVRDEGQYQCIIIYGVAWDYKY
        CD80 (51) --VLTMMSGDMNI-WPEYKNRTIFDIT----NNLSIVILALRPSDEGTYECVVLKYEKDAFKR
        CD86 (62) EVYLGKEKFD-SV-HSKYMGRTSFDSD-----SWTLRLHNLQIKDKGLYQCIIHHKKPTGMIR
      CTLA-4 (60) EVCAATYMMGNEL-TFLD--DSICTGTS-SGNQVNLTIQGLRAMDTGLYICKVELMYPPPY--
        CD28 (67) EVCVVYGNYSQQL-QVYSKTGFNCDGKL-GNESVTFYLQNLYVNQTDIYFCKIEVMYPPPYLD
    Siglec-1 (68) RQVVSHSADPKLV-EARFRGRTEFMGNP-EHRVCNLLLKDLQPEDSGSYNFRFEISEVNRWSD
    Siglec-2 (61) GTRLYESTKDGKV--PSEQKRVQFLGD--KNKNCTLSIHPVHLNDSGQLGLRMESKTEKWMER
    Siglec-3 (80) DSFVATNKLDQEV-QEETQGRFRLLGDP-SRNNCSLSIVDARRRDNGSYFFRMERG-STKYSY
    Siglec-4 (75) YPPVVFKSRTQVV-HESFQGRSRLLGDL-GLRNCTLLLSNVSPELGGKYYFRGD--------
    Siglec-5 (80) AEVVATNNPDRRV-KPETQGRFRLLGDV-QKKNCSLSIGDARMEDTGSYFFRVERGRDVKYSY
    Siglec-6 (76) DVPVATNDPDEEV-QEETRGRFHLLWDP-RRKNCSLSIRDARRRDNAAYFFRL---------
    Siglec-7 (81) KAPVATNNPAWAV-QEETRDRFHLLGDP-QTKNCTLSIRDARMSDAGRYF------------
    Siglec-8 (82) DAPVATNNPDREV-QAETQGRFQLLGDI-WSNDCSLSIRDARKRDKGSYF------------
    Siglec-9 (78) DAPVATNNPARAV-WEETRDRFHLLGDP-HTKNCTLSIRDARRSDAGRYFFRMEKG-SIKWNY
   Siglec-10 (81) GAPVATNHQSREV-EMSTRGRFQLTGDP-AKGNCSLVIRDAQMQDESQYFFRVE---------
   Siglec-11 (81) GAPVATNNQSREV-EMSTRDRFQLTGDP-GKGSCSLVIRDAQREDEAWYFFRVE---------
 Siglec-12-A (80) NIPVATNNPARAV-QEETRDRFHLLGDP-QNKDCTLSIRDTRESDAGTYVFCVERG-NMKWNY
 Siglec-12-B (78) DIPVATNTPSGKV-QEDTHGRFLLLGDP-QTNNCSLSIRDARKGDSGKYYFQVERG-SRKWNY
   Siglec-14 (81) AEVVATNNPDRRV-KPETQGRFRLLGDV-QKKNCSLSIGDARMEDTGSYFFRVERGRDVKYSY
   Siglec-15 (66) RCAAARGSELCQT-ALSLHGRFRLLGN-PRRNDLSLRVERLALADDRRYFCRVEFAGDVHDRY
   Siglec-16 (73) GAPVATNNQSREV-AMSTRDRFQLTGDP-GKGSCSLVIRDAQREDEAWYFFRVE---------
```

FIG 3

DISRUPTION OF CD28-SIALOSIDE LIGAND COMPLEXES TO ENHANCE T CELL ACTIVATION

CROSS-REFERENCE TO RELATED APPLICATIONS

The subject patent application claims the benefit of priority to U.S. Provisional Patent Application No. 63/054,516 (filed Jul. 21, 2020; now pending). The full disclosure of the priority application is incorporated herein by reference in its entirety and for all purposes.

STATEMENT OF GOVERNMENT SUPPORT

This invention was made with government support under Contract No. AI050143 awarded by the National Institutes of Health. The government has certain rights in this invention.

BACKGROUND OF THE INVENTION

Immune responses by T cells are initiated by their interaction with antigen presenting cells (APCs), which involves binding of the T cell receptor (TCR) to antigenic peptides presented on major-histocompatibility complex (MHC) displayed on the surface of the APC. This antigen-specific "first signal" is operative for both cytotoxic T cells ($CD8^+$) and helper T cells ($CD4^+$), where antigen is recognized in the context of MHC type I and MHC type II molecules, respectively. For optimal activation, a 'second signal' is required that involves engagement of co-receptors on the T cell with protein ligands on the APC. This 'second signal' is mediated by engagement of the co-receptor CD28 on the T cell with one of two related protein ligands on the APC called CD80 (B7-1) or CD86 (B7-2), and sometimes collectively called CD80/CD86 or B7. Ligation of the TCR to MHC and CD28 to CD80/86 forms the T cell-APC immunological synapse, which is necessary for antigen-specific expansion of naïve T cell populations and differentiation into effector cells.

T cells also express inhibitory co-receptors (e.g. PD-1, CTLA-4) that can negatively regulate T cell activation when they are recruited to the immunological synapse. These receptors are recruited when their respective ligands are expressed on the APC. Exemplary ligands of PD-1 are PD-L1 and PD-L2. Remarkably, CTLA-4 uses the same ligands as CD28 (CD80/CD86), such that CD28 competes with CTLA-4 for ligands that recruit them to the immunological synapse. Notably, tumor cells often express the ligands of PD-1 and CTLA-4, resulting in their recruitment to the immunological synapse upon contact of a tumor-specific T cell with a tumor cell presenting MHC bound tumor antigen. In this way, tumor cells are able to suppress immune responses that would otherwise attack them. Thus, blockade of the interactions of the inhibitory receptor with their ligands has had profound implications for oncology, with therapeutics such as pembrolizumab/nivolumab/cemiplimab (anti-PD-1), atezolizumab/avelumab/durvalumab (anti-PD-L1), and ipilimumab (anti-CTLA-4) enhancing anti-cancer T cell activity and in some patients resulting in remarkable tumor regression.

There is a need in the art for additional and more effective means for suppressing T cell inhibitory receptors and enhancing T cell responses in immunotherapies. The present invention is directed to this and other unmet needs in the art.

SUMMARY OF THE INVENTION

In one aspect, the invention provides methods for enhancing T cell activation and expansion. The methods entail contacting a population of non-cancerous T cells with a targeting agent-enzyme conjugate. The targeting agent-enzyme conjugate contains (a) a targeting moiety that specifically binds a cell surface molecule on T cells, and (b) a sialidase or enzymatically active fragment thereof. The targeting agent-enzyme conjugate enhances activation and expansion of the T cells by specifically degrading sialic acids on the surface of the cells. In some embodiments, the targeting moiety in the conjugate is an antibody or antigen binding fragment thereof. In some embodiments, the targeted T cell surface molecule is an inhibitory co-receptor. In some of these embodiments, the targeted T inhibitory co-receptor is PD-1, CTLA-4, TIM-3, TIGIT or LAG-3. In some of these embodiments, the targeting agent is a blocking antibody or antigen-binding fragment thereof that specifically binds to the inhibitory co-receptor. In various embodiments, the employed blocking antibody can be Pembrolizumab, Nivolumab, Cemiplimab, Ipilimumab and Tremelimumab.

In some methods, the sialidase in the employed conjugate is human neuraminidase 1 (Neu1), neuraminidase 2 (Neu2), neuraminidase 3 (Neu3), or neuraminidase 4 (Neu4). In some methods, the population of T cells are contacted with the targeting agent-enzyme conjugate in vivo. In some other methods, the population of T cells are contacted with the targeting agent-enzyme conjugate ex vivo. In some methods, the population of T cells to be activated are $CD8^+$ T cells or $CD4^+$ T cells or $CD8^+CD4^+$ T cells. Some methods of the invention are directed to activation and expansion of a population of naïve T cells. Some methods of the invention are directed to activation and expansion of a population of exhausted T cells. In some embodiments, the population of T cells are contacted with the conjugate in the presence of a specific antigen. In some of these embodiments, the specific antigen is presented by an antigen presenting cell.

In a related aspect, the invention provides methods for stimulating or eliciting a T cell immune response in a subject. These methods involve administering to the subject a targeting agent-enzyme conjugate that contains (a) a targeting moiety that specifically binds a cell surface molecule on T cells, and (b) a sialidase or enzymatically active fragment thereof. The administered conjugate specifically degrades sialic acids on the surface of a group of T cells in the subject, thereby stimulating a T cell immune response in the subject. Some of these methods are directed to subjects who are not afflicted with a T cell lymphoma. Some of these methods are directed to subjects who are suffering from a solid tumor or an infection (e.g., a bacterial or viral infection). In some of these embodiments, other than a solid tumor or an infection, the subjects do not have or are not suspected of having a T cell related tumor (e.g., T cell lymphoma).

In some embodiments, the T cell surface molecule in the subject to be targeted with the administered conjugate is an inhibitory co-receptor expressed on the surface of a T cell. In some of these embodiments, the targeting moiety in the administered conjugate is a blocking antibody or antigen-binding fragment thereof that specifically binds to the inhibitory co-receptor. In some embodiments, the sialidase in the administered conjugate is human neuraminidase 1 (Neu1), neuraminidase 2 (Neu2), neuraminidase 3 (Neu3), or neuraminidase 4 (Neu4). In various embodiments, the targeting agent-enzyme conjugate is administered to the subject via a pharmaceutical composition.

In another aspect, the invention provides targeting agent-enzyme conjugates. These conjugates contain (a) a targeting moiety that specifically recognizes a cell surface molecule on a T cell, and (b) a sialidase or enzymatically active fragment thereof. Some targeting agent-enzyme conjugates are intended for administration to subjects with tumors. In some of these embodiments, the cell surface molecule to be targeted is not expressed on the surface of tumor cells in the patient who is to receive the conjugate. In some targeting agent-enzyme conjugates of the invention, the targeting moiety is an antibody or antibody fragment that binds to the cell surface molecule. In some targeting agent-enzyme conjugates of the invention, the targeting moiety is conjugated to the sialidase enzyme covalently. In some embodiments, the T cell surface molecule to be targeted is PD1, CTLA-4, TIM-3, TIGIT or LAG-3. In various embodiments, the sialidase to be used in the conjugates can be a human sialidase, a bacterial sialidase (e.g., a *Salmonella typhimurium* sialidase), or a viral sialidase. In some embodiments, the sialidase in the conjugates is human neuraminidase 1 (Neu1), neuraminidase 2 (Neu2), neuraminidase 3 (Neu3), or neuraminidase 4 (Neu4).

Some specific sialidase-containing conjugates of the invention are directed to targeting PD1. Any anti-PD1 antibody or antibody fragment thereof can be used as the targeting moiety in the construction of these antibody conjugates. These include, e.g., Pembrolizumab (Keytruda), Nivolumab (Opdivo) and Cemiplimab (Libtayo). In some of these embodiments, the sialidase (e.g., a human sialidase or a bacterial sialidase) can be fused non-selectively to the anti-PD1 antibody, e.g., to lysine side chains of the antibody. In some other embodiments, the sialidase can be fused site-specifically to the antibody, e.g., to the C-terminus of a heavy chain of the antibody. In some embodiments, the sialidase antibody conjugates targeting a T cell surface molecule are capable of enhancing sialidase mediated removal of sialic acids from a T cell expressing the cell surface molecule by at least 5 fold, relative to a T cell not expressing the cell surface molecule.

A further understanding of the nature and advantages of the present invention may be realized by reference to the remaining portions of the specification and claims.

DESCRIPTION OF THE DRAWINGS

FIG. 3. V-set domain alignment of CD28, CTLA-4, PD-1 and their B7 ligands with all human Siglecs (SEQ ID NOs:1-23, respectively). The arrow denotes conserved Arg in Siglecs. Coffee multiple sequence alignment server was used to generate the data. Sequence alignment scores in parentheses. Only a portion of the alignment is shown.

As illustrated in FIG. 14, *Salmonella typhimurium* sialidase (S) was coupled to anti-human PD-1 (αhPD1) clones 1H3 and 409A11 yielding two corresponding αPD1-S conjugates. The αPD1-S conjugates were each assessed for their ability to remove sialic acids from Jurkat T cells and Jurkat T cells expressing PD-1-green fluorescent protein (Jurkat-PD1-GFP). Jurkat and Jurkat-PD1-GFP cells were mixed 1:1 (40,000 cells each) in phosphate buffered saline (PBS) containing calcium and magnesium, 10 mg/ml bovine serum albumin (BSA) and serial dilutions of αPD1-S for 20 min at 37° C. Cells were pelleted by centrifugation and washed with PBS/BSA to remove sialidase. Cells were then incubated for 30 min with one of three different biotinylated lectins precomplexed with streptavidin-phycoerythrin (PE) to track loss of sialic acids including: *Sambucus nigra* agglutinin (SNA) that recognizes NeuAcα2-6Gal linkages lost by desialylation; (B) peanut agglutinin (PNA) that recognizes Galβ1-3GalNAc revealed by loss of sialic acid from the NeuAcα2-3Galβ1-3GalNAc sequence; and (C) *Maackia amurensis* agglutinin II (MAA-II) that recognizes NeuAcα2-3Gal linkages lost by desialylation. Cells were then analyzed by flow cytometry to detect the level of lectin staining for Jurkat and Jurkat-PD1-GFP T cells. Data shown compare the efficiency of αPD1-S mediated desialylation of Jurkat and Jurkat-PD1-GFP T cells as detected by the three lectins: (A) SNA, (B) PNA, and (C) MAA-II. For each of the three lectins (A, B, and C) results obtained with αhPD1-S (409A11) are shown on the left and results obtained with αhPD1-S (1H3) are shown on the right. At the top of each panel are shown examples of flow cytometry contour plots for Jurkat and Jurkat-PD1-GFP T cell mixtures treated with no αPD1-S and a concentration of αPD1-S that showed enhanced removal of sialic acid from Jurkat-PD-1-GFP cells. Graphs at the bottom of each panel show the fraction of T cells stained by the respective lectin after treatment by the αPD1-S over the entire range of concentrations used expressed as sialidase activity in the reaction in international units (U/ml=μmol $min^{-1}$ $mL^{-1}$). Results show that regardless of the lectin used for detection, SNA (A), PNA (B), and MAA-II (C), the αPD1-S conjugates exhibited enhanced desialylation of the Jurkat T cells expressing PD1-GFP by over 100 fold.

DETAILED DESCRIPTION

I. Overview

Figure 1:
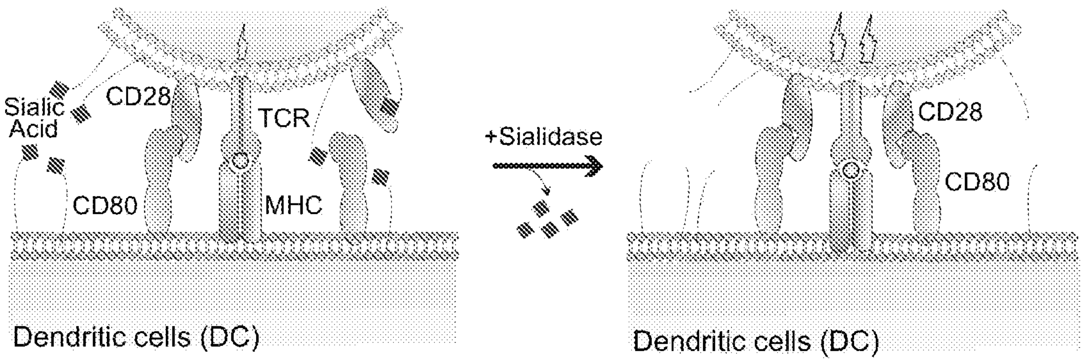
FIG. 1 is a schematic of CD28-mediated enhancement of T cell activation following treatment by sialidase.

The present invention is predicated in part on the studies undertaken by present inventors to uncover the molecular basis for the enhancement of T cell activation by neuraminidase. As detailed herein, the inventors found that CD28 on the T cell binds to sialic acid-containing ligands in a manner that competes with binding to its activatory protein ligand CD80/CD86 (FIG. 1). It was observed that sialic acids on the T cell (cis sialic acids) or on the APC (trans sialic acids) compete with CD80 for binding to CD28. Thus, removing sialic acids with neuraminidase (also called sialidase) enhances CD28 engagement on the T cell with CD80 on the APC, which in principle increases its recruitment to the immunological synapse and results in enhanced activation of the T cell. In some related studies, the inventors generated antibody-sialidase conjugates to examine desialylation activities of T-cell targeting sialidases. It was observed that conjugates formed of an anti-PD-1 antibody and a sialidase were able to selectively enhance desialylation of PD-1-expressing T cells.

In accordance with these studies, the invention accordingly provides targeting agent-enzyme conjugates that contain a targeting agent that specifically recognizes a T cell surface molecule or antigen and an enzyme that degrades sialic acid. The invention also provides methods for enhancing T cell activation and expansion, which entail the use of such targeting agent-enzyme conjugates to activate T cells (e.g., native T cells, non-cancerous T cells or exhausted T cells). The invention additionally provides therapeutic methods for stimulating a T cell-mediated immune response in a subject. These methods require administration to a subject (e.g., a subject afflicted with an infection) a targeting agent-enzyme conjugate described herein.

Recent reports have suggested that sialic acid containing ligands on tumor cells would serve as ligands for inhibitory Siglecs on immune cells. A strategy for targeting tumor cells by tethering a bacterial neuraminidase/sialidase to trastuzumab, an antibody to a cancer antigen, HER2, have been reported. See, e.g., Xiao et al., Proc Natl Acad Sci USA 113, 10304-9, 2016; Gray et al., Chemrxiv, 8187146.v2, doi:10.26434, 2019; Gray et al. Nat Chem Biol 16, 1376-1384, 2020; and Stanczak, M. A. et al. bioRxiv, 2021.2004.2011.439323. Notably, this reported strategy aims to remove sialic acids on the tumor cell to prevent recruitment of inhibitory Siglecs on the immune cell to the immunological synapse with the tumor cell. As described below, this is in contrast to the conjugates of the present invention where sialic acids are removed from the T cell and APC to promote the recruitment of the activatory receptor CD28 to the immunological synapse.

Unless otherwise specified herein, the methods and compositions described herein can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Sambrook et al., Molecular Cloning: A Laboratory Manual, Cold Spring Harbor Press, N.Y., (3rd ed., 2000); Brent et al., Current Protocols in Molecular Biology, John Wiley & Sons, Inc. (ringbou ed., 2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

The following sections provide more detailed guidance for practicing the invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1st ed., 1992); *Oxford Dictionary of Biochemistry and Molecular Biology*, Smith et al. (Eds.), Oxford University Press (revised ed., 2000); *Encyclopedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3rd ed., 2002); *Dictionary of Chemistry*, Hunt (Ed.), Routledge (1st ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4th ed., 2000). Further clarifications of some of these terms as they apply specifically to this invention are provided herein.

Unless otherwise noted, the expression “at least” or “at least one of” as used herein includes individually each of the recited objects after the expression and the various combinations of two or more of the recited objects unless otherwise understood from the context and use. The expression “and/or” in connection with three or more recited objects should be understood to have the same meaning unless otherwise understood from the context.

The term “antibody” also synonymously called “immunoglobulins” (Ig), or “antigen-binding fragment” refers to polypeptide chain(s) which exhibit a strong monovalent, bivalent or polyvalent binding to a given antigen, epitope or epitopes. Unless otherwise noted, antibodies or antigen-binding fragments used in the invention can have sequences derived from any vertebrate species. They can be generated using any suitable technology, e.g., hybridoma technology, ribosome display, phage display, gene shuffling libraries, semi-synthetic or fully synthetic libraries or combinations thereof. Unless otherwise noted, the term “antibody” as used in the present invention includes intact antibodies, antigen-binding polypeptide fragments and other designer antibodies that are described below or well known in the art (see, e.g., Serafini, J Nucl. Med. 34:533-6, 1993).

An intact “antibody” typically comprises at least two heavy (H) chains (about 50-70 kD) and two light (L) chains (about 25 kD) inter-connected by disulfide bonds. The recognized immunoglobulin genes encoding antibody chains include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Each heavy chain of an antibody is comprised of a heavy chain variable region ($V_H$) and a heavy chain constant region. The heavy chain constant region of most IgG isotypes (subclasses) is comprised of three domains, $C_{H1}$, $C_{H2}$ and $C_{H3}$, some IgG isotypes, like IgM or IgE comprise a fourth constant region domain, $C_{H4}$. Each light chain is comprised of a light chain variable region ($V_L$) and a light chain constant region. The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system and the first component (Clq) of the classical complement system.

The $V_H$ and $V_L$ regions of an antibody can be further subdivided into regions of hypervariability, also termed complementarity determining regions (CDRs), which are interspersed with the more conserved framework regions (FRs). Each $V_H$ and $V_L$ is composed of three CDRs and four FRs, arranged from amino-terminus to carboxyl-terminus in the following order: FR1, CDR1, FR2, CDR2, FR3, CDR3, FR4. The locations of CDR and FR regions and a numbering system have been defined by, e.g., Kabat et al., *Sequences of Proteins of Immunological Interest*, U.S. Department of Health and Human Services, U.S. Government Printing Office (1987 and 1991).

An "antibody-based binding protein", as used herein, may represent any protein that contains at least one antibody-derived $V_H$, $V_L$, or $C_H$ immunoglobulin domain in the context of other non-immunoglobulin, or non-antibody derived components. Such antibody-based proteins include, but are not limited to (i) Fe-fusion proteins of binding proteins, including receptors or receptor components with all or parts of the immunoglobulin $C_H$ domains, (ii) binding proteins, in which $V_H$ and or $V_L$ domains are coupled to alternative molecular scaffolds, or (iii) molecules, in which immunoglobulin $V_H$, and/or $V_L$, and/or $C_H$ domains are combined and/or assembled in a fashion not normally found in naturally occurring antibodies or antibody fragments.

"Binding affinity" is generally expressed in terms of equilibrium association or dissociation constants ($K_A$ or $K_D$, respectively), which are in turn reciprocal ratios of dissociation and association rate constants ($k_{off}$ and $k_{on}$, respectively). Thus, equivalent affinities may correspond to different rate constants, so long as the ratio of the rate constants remains the same. The binding affinity of an antibody is usually be expressed as the $K_D$ of a monovalent fragment (e.g. a $F_{ab}$ fragment) of the antibody, with $K_D$ values in the single-digit nanomolar range or below (subnanomolar or picomolar) being considered as very high and of therapeutic and diagnostic relevance.

As used herein, the term "binding specificity" refers to the selective affinity of one molecule for another such as the binding of antibodies to antigens (or an epitope or antigenic determinant thereof), receptors to ligands, and enzymes to substrates. Thus, all monoclonal antibodies that bind to a particular antigenic determinant of an entity (e.g., a specific epitope of ROR1 or ROR2) are deemed to have the same binding specificity for that entity.

The term "Antibody Drug Conjugate", or "ADC" refers to an antibody to which a therapeutically active substance (e.g., a toxin or an enzyme) or an active pharmaceutical ingredient (API) has been conjugated (e.g., covalently coupled), such that the therapeutically active substance or an active pharmaceutical ingredient (API) can be targeted to the binding target of the antibody to exhibit its pharmacologic function. The attachment of a therapeutically active substance, an active pharmaceutical ingredient or a cellular toxin can be performed in a non-site specific manner using standard chemical linkers that couple payloads to lysine or cysteine residues, or, preferably the conjugation is performed in a site-specific manner, that allows full control of conjugation site and drug to antibody ratio (DAR) of the ADC to be generated.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "contacting" has its normal meaning and refers to combining two or more agents (e.g., polypeptides or phage), combining agents and cells, or combining two populations of different cells. Contacting can occur in vitro, e.g., mixing an antibody and a cell or mixing a population of antibodies with a population of cells in a test tube or growth medium. Contacting can also occur in a cell or in situ, e.g., contacting two polypeptides in a cell by co-expression in the cell of recombinant polynucleotides encoding the two polypeptides, or in a cell lysate. Contacting can also occur in vivo inside a subject, e.g., by administering an agent to a subject for delivery the agent to a target cell.

A "humanized antibody" is an antibody or antibody fragment, antigen-binding fragment, or antibody-based binding protein comprising antibody $V_H$ or $V_L$ domains with a homology to human $V_H$ or $V_L$ antibody framework sequences having a T20 score of greater than 80, as defined by defined by Gao et al. (2013) BMC Biotechnol. 13, pp. 55.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, FASTA, and TFASTA in the Wisconsin Genetics Software Package, Genetics Computer Group, Madison, WI); or by manual alignment and visual inspection (see, e.g., Brent et al., *Current Protocols in Molecular Biology*, John Wiley & Sons, Inc. (ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

Sialidases (neuraminidases) are glycoside hydrolase enzymes that catalyze the cleavage of glycosidic linkages between a sialic acid residue and a hexose or hexosamine residue at the nonreducing terminal of oligosaccharides in glycoproteins, glycolipids, and proteoglycans. Various sialidases have been identified that catalyze the hydrolysis of terminal sialic acid residues from virions and from host cell receptors.

The term "subject" or "patient" refers to human and non-human animals (especially non-human mammals). The term "subject" is used herein, for example, in connection with therapeutic methods, to refer to human or non-human subjects. Examples of non-human subjects include, but are not limited to, cows, horses, sheep, pigs, cats, dogs, mice, rats, rabbits, guinea pigs, monkeys.

The terms "treat," "treating," "treatment," and "therapeutically effective" used herein do not necessarily imply 100% or complete treatment. Rather, there are varying degrees of treatment recognized by one of ordinary skill in the art as having a potential benefit or therapeutic effect. In this respect, the inventive method can provide any amount of any level of treatment. Furthermore, the treatment provided by the inventive method can include the treatment of one or more conditions or symptoms of the disease being treated.

A "vector" is a replicon, such as plasmid, phage or cosmid, to which another polynucleotide segment may be attached so as to bring about the replication of the attached segment. Vectors capable of directing the expression of genes encoding for one or more polypeptides are referred to as "expression vectors".

The term "agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" or "derivative" is used herein to refer to a molecule that structurally resembles a reference molecule (e.g., a known sialidase) but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs to identify variants of known compounds having improved traits is an approach that is well known in pharmaceutical chemistry.

Antigen presenting cells refer to a type of immune cell that enables a T lymphocyte (T cell) to recognize an antigen and mount an immune response against the antigen. APCs include (but are not limited to) macrophages, dendritic cells, and B lymphocytes (B cells).

The term antigen broadly refers to a molecule that can be recognized by the immune system. It encompasses proteins, polypeptides, polysaccharides, small molecule haptens, nucleic acids, as well as lipid-linked antigens (polypeptide- or polysaccharide-linked lipids.

The term "immune conjugate" as used herein refers to a complex in which a sialidase enzyme is coupled to targeting agent or moiety for an immune cell surface antigen. In some preferred embodiments, the targeting agent is an antibody or antigen-binding fragment thereof. In some preferred embodiments, the targeting agent specifically binds to a T cell surface molecule. The sialidase can be coupled directly to the targeting agent via an appropriate linking chemistry. Alternatively, the enzyme can be linked indirectly to the targeting agent, e.g., via a third molecule such as a spacer. The linkage between the targeting agent and the enzyme can be either covalent or non-covalent. Alternatively, the targeting agent and enzyme can also be expressed as a single engineered fusion protein.

As used herein, T cell inhibitory co-receptors refers to a group of molecules expressed on the surface of T cells that play an inhibitory role in the activation of T cells by antigen-presenting cells (APCs). The activation of naïve T cells requires both the stimulation of the T-cell receptor (TCR) by a major histocompatibility complex (MHC)-peptide complex and co-stimulatory signaling by co-stimulatory receptors (e.g., CD28) with their corresponding ligands on antigen-presenting cells (APCs). T cell inhibitory co-receptors negatively regulate TCR driven signals and therefore T-cell activation. Examples of T cell inhibitory co-receptors include CTLA-4 and PD1.

Administration "in conjunction with" one or more other therapeutic agents includes simultaneous (concurrent) and consecutive administration in any order.

T-cell exhaustion refers to a progressive loss of effector function due to prolonged antigen stimulation, characteristic of chronic infections and cancer. In addition to continuous antigen stimulation, antigen presenting cells and cytokines present in the microenvironment can also contribute to this exhausted phenotype. Exhaustion has been mostly described for $CD8^+$ T cells responses although $CD4^+$ T cells have also been reported to be functionally unresponsive in several chronic infections, Exhausted T cells typically have elevated expression of inhibitory co-receptors such as PD-1, CTLA-4 and Tim-3, and reversal of T cell exhaustion has been shown by blocking these co-inhibitory receptors.

III. Sialidase-Containing Drug Conjugates for Targeting Immune Cells

The invention provides immune cell targeting drug conjugates for tuning T cell activity (e.g., promoting T cell activation) by disrupting a protein-glycan interaction with a modular targeting agent-sialidase conjugate compound. The sialidase-containing conjugates are intended to degrade sialic acid on the immunological synapse surface of T cells and antigen-presenting cells (APCs). In general, the drug conjugates contain a targeting agent or compound (e.g., an antibody) that specifically recognizes a cell surface molecule or antigen on the immune cells. In the conjugates, a sialidase (e.g., neuraminidase) or an enzymatically active fragment thereof is conjugated, directly or via a suitable linker moiety, to the targeting agent. Depending on the specific targeting agent used, the conjugation can be either covalent or non-covalent as detailed herein.

Any sialidase that is capable of degrading sialic acid molecules can be used in the drug conjugates of the invention. Sialidases (neuraminidases) are a large family of enzymes found in a range of organisms. A well-known neuraminidase is the influenza virus neuraminidase, a drug target for the prevention of the spread of influenza infection. The viral neuraminidases are frequently used as antigenic determinants found on the surface of the influenza virus and paramyxoviruses (see, e.g., Thompson et al., Curr. Opin. Virol. 34: 117-129, 2019). Some variants of the influenza neuraminidase confer more virulence to the virus than others. Other sialidases are found in bacteria, with over 70 bacterial species reported to produce sialidases, many of which are pathogenic or commensal bacterial strains in mammals. See, e.g., Sudhakara et al., Pathogens 8: 39-49, 2019; and Roggentin et al., Mol. Microbiol. 9: 915-921, 1993). Common bacterial sialidases used as reagents in biological research are those from *Vibrio cholerae, Clostridium perfringens*, and *Salmonella typhimurium*. Other sialidases are found in mammalian cells, which have a range of functions. Preferably, the sialidase used in the invention is a mammalian sialidase (e.g., a human sialidase) or enzymatically active fragment thereof. At least four mammalian sialidase homologues have been identified from human genome, Neu1, Neu2, Neu3, and Neu4. Their structures and functions have all been characterized in the literature. See, e.g., Pshezhetsky et al., Nat. Genet. 15: 316-20, 1997; Monti et al., Genomics 57: 137-143, 1999; Tringali et al., J. Biol. Chem. 279: 3169-3179, 2004; Wada et al., Biochem. Biophys. Res. Commun. 261: 21-7, 1999; Bigi et al., Glycobiol. 20: 148-57, 2010; Miyagi et al., Glycobiol. 22: 880-896, 2012; and Lipnicanova et al., Int. J. Biol. Macromol. 148: 857-868, 2020. In some of these preferred embodiments, the drug conjugates of the invention contain Neu1 as exemplified herein. In some other embodiments, a viral sialidase or a bacterial sialidase can be used in the conjugates, e.g., a *Salmonella typhimurium* sialidase as exemplified herein.

The targeting agents for constructing the conjugates of the invention can be any molecules that bind to a surface antigen or molecule on immune cells, e.g., T cells or APCs. Preferably, the employed targeting agent would not interfere or substantially reduce the normal biological function of the immune cell, e.g., T cell activation or antigen presentation by APCs. Some embodiments of the invention are directed drug conjugates containing a sialidase that is conjugated to a T cell targeting agent. In some embodiments, the employed targeting agent can be an antibody or antigen-binding fragment (e.g., Fab) that specifically recognizes a T cell-specific surface marker. In some embodiments, the T cell surface molecule to be targeted is an inhibitory co-receptor expressed on T cells, e.g., PD1 or CTLA-4.

There are several advantages associated with using the sialidase containing immune cell targeting drug conjugates of the invention. Current T cell activation-related immunotherapies target inhibitory protein-protein interactions (i.e. PD-1/PD-L1/PD-L2) that occur between T cells and APCs upon formation of an immunological synapse. The conjugates of the invention and related methods are directed to enhancing T cell response by targeting cell surface sialosides on immune cells. By degrading sialic acids on T cells and APCs which block binding of T cell activatory coreceptor CD28 to its cognate ligand on APCs, CD80/86, the sialidase containing drug conjugates promote binding of CD28 to CD80/86 resulting in enhancement of T cell activation and proliferation. In addition, the drug conjugates of the invention enable targeting of neuraminidase to a T cell to promote potent CD28 signaling by a mechanism that is synergistic to blocking inhibitory receptors such as PD-1 and CTLA-4 (see Example 6).

In addition, T cell targeting sialidase antibody conjugates of the invention have demonstrated unexpected and surprisingly potent activities in desialylation of T cells. As exemplification, it was shown that PD1-targeting sialidase antibody conjugates are able to selectively enhance desialylation of PD1-expressing T cells (see, e.g., Example 9). Importantly, the exemplified PD1-targeting sialidase antibody conjugates are about 100 times or more active at desialylating T cells expressing PD1 than T cells not expressing PD1 (see, e.g., Example 9 below). In various embodiments, the sialidase-containing antibody conjugates of the invention that target a T cell surface molecule (e.g., PD1) are capable of enhancing sialidase mediated removal of sialic acids from T cells expressing the cell surface molecule by at least 5, 10, 25, 50, 100 or more folds, relative to T cells not expressing the surface molecule.

The sialidase containing immune cell targeting drug conjugates of the invention are useful to enhance antigen-specific T cell mediated immune cells in vivo. The drug conjugates of the invention can be readily employed in many therapeutic applications, e.g., enhancing immune responses against various cancers where immune responses are suppressed by inhibitory receptors. As exemplification, particularly useful conjugates contain a sialidase that is targeted by known therapeutic antibodies that specifically recognize T cell inhibitory receptors PD1 or CTLA-4. The targeting antibodies can block engagement of the inhibitory receptor with its corresponding ligand on the cancer cell, preventing its recruitment to the immunological synapse, thereby 'releasing the brakes' on the T cell for mounting an attack on the tumor cell. By conjugating these antibodies to a neuraminidase, there would be further enhancement of activation by destroying sialic acids on the T cell, allowing more efficient binding of CD28 to its ligand (CD80/86) on the cancer cell or other APCs. Such a synergistic effect can be achieved in both $CD8^+$ and $CD4^+$ T cells and their interactions with any APC.

IV. T Cell Surface Molecules for Targeting

The sialidase-containing antibody conjugates are intended to degrade sialic acid on T cells. In a broad sense, any cell surface molecule or antigen on T cells can be the target to which the conjugates target. In some of these embodiments, the cell surface molecule to be targeted is a T cell-specific surface marker. In some embodiments, the T cell-specific surface marker is primarily expressed by normal, healthy naïve or activated T cells without substantial expression on tumor cells and/or other types of cells. Some embodiments of the invention are directed to administration of a sialidase-containing drug conjugate to patients with cancer or tumors where the sialidase-drug conjugate does not bind to the tumor cells. In some of these embodiments, the surface marker to be targeted is not substantially or primarily expressed or present on the surface of tumor cells in the intended patients. In some embodiments, the surface marker to be targeted is not substantially or primarily expressed or present on the surface of solid tumors.

Some examples of T cell surface markers that can be targeted with the sialidase-containing conjugates of the invention are shown in Table 1. In some embodiments, the T cell surface marker to be targeted is not activatory for T cell activation or function. As exemplified in Table 1, such T cell surface markers include CD5, CD&, CD30, CD39, CD52, A2aR, PD-1 and CTLA-4. In some embodiments, the cell surface molecule is expressed by both T cells and APCs. These include some checkpoint inhibitors described herein, e.g., PD1, CTLA-4 and TIGIT. In some embodiments, the cell surface molecule to be targeted is a T cell specific surface marker.

Some drug conjugates of the invention are intended to target T cells. Preferably, the cell surface molecule to be targeted is specific to T cells. Many T cell specific surface receptors or molecules are known in the art. In various embodiments, suitable T cell surface molecules to be targeted include, but are not limited to CD3 (non-blocking), CD4 (non-blocking), CD8a (non-blocking), CD40L (non-blocking), CD45RA, CD45RB, CD62L, CD152 (CTLA-4), CD127, CD279 (PD-1). When T cell surface markers required for T cell activation or normal immune response are targeted, (e.g., CD3, CD4, CD8 and CD40), the employed targeting agents are preferably non-blocking.

TABLE 1

T cell markers for targeted delivery of antibody-sialidase conjugates to the surface of the cell

| T cell protein/marker | Expression | Inhibitory or Activatory |
|---|---|---|
| CD3 | Most T cell subsets | Activatory |
| CD4 | Helper and regulatory T cells | Activatory |
| CD5 | All T cell subsets | Inhibitory |
| CD6 | Highest on naïve T cells | Activatory |
| CD7 | Most T cell subsets | Neither (involved in adhesion) |
| CD8a | Cytotoxic T cells | Activatory |
| CD30 | Subset of activated T cells | Inhibitory |
| CD37 | Most T cell subsets | Inhibitory when KO, activatory when ligated with Ab |
| CD39 | TILs, regulatory, and memory T cells | Inhibitory |
| CD40L | Helper T cells | Activatory |
| CD45RA | Naïve T cells | Unclear |
| CD45RB | Naïve T cells | Activatory |
| CD48 | Most T cell subsets | Activatory |
| CD52 | Most T cell subsets | Inhibitory |
| CD62L | Multiple subsets including naïve | Neither (roles in leukocyte adhesion) |
| CD96 | Most T cell subsets | Both inhibitory and activatory effects reported |
| CD97 | Increased expression on activated T cells | Activatory |
| CD99 | Highest on immature T cells | Activatory |
| CD122 (IL-2 receptor subunit beta) | $CD8^+$ T cell subsets | Activatory |
| CD127 | Memory and effector T cells | Activatory |
| CD132 (IL-2 receptor subunit gamma) | Most T cell subsets | Activatory |
| CD162 (PSGL-1) | Most T cell subsets | Adhesion but also inhibitory |
| CD225 (IFITM-1) ? | Unclear | Unclear |
| CD244 (SLAM, 2B4) | $CD8^+$ T cell and gamma delta subsets | Both inhibitory and activatory effects reported |
| A2aR | $CD4^+$ and $CD8^+$ T cell subsets and TILs | Inhibitory |
| CS1 (SLAMF7, CD319) | Unclear | Activatory |
| CTLA-4 | Exhausted T cells | Inhibitory |
| PD-1 | Exhausted T cells | Inhibitory |
| TIRC7 | Activated T cells | Activatory |

In some embodiments, the targeting agent (e.g., an antibody) on the sialidase-containing drug conjugates of the invention specifically binds to an inhibitory co-receptor that is expressed on the surface of T cells. Many inhibitory co-receptors on T cells have been identified, including T-lymphocyte-associated protein 4 (CTLA-4), Programmed cell death protein 1 (PD-1), T-cell immunoglobulin and mucin-domain containing-3 (TIM-3), T-cell immunoreceptor with Ig and ITIM domains (TIGIT), and lymphocyte-activation protein 3 (LAG-3). See, e.g., Anderson et al., Immunity 44:989-1004, 2016; Jin et al., Curr. Top. Microbiol. Immunol. 350:17-37, 2011; and Gardner et al., Am. J. Transplant. 14:1985-91, 2014. The inhibitory co-receptors play an important role in several T-cell subsets including activated T cells, regulatory T cells, and exhausted T cells. In activated T cells, inhibitory co-receptors control and contract the expanded T-cell population. In regulatory T cells (Tregs), inhibitory co-receptors, such as CTLA-4 and PD-1, promote the suppressive function of Tregs. As noted above, some of the T cell inhibitory co-receptors are also expressed on APCs. Thus, sialidase-containing drug conjugates that target one of these surface molecules (e.g., PD1, CTLA-4 and TIGIT) are expected to deliver sialidase activity to both T cells and APCs upon their attachment to these cells.

IV. Targeting Agents

The immune stimulating drug conjugates of the invention contains a targeting agent that specifically recognizes a cell surface molecule or antigen that is expressed or present on immune cells (e.g., T cells). The targeting agent can be a compound of any chemical class. These include, e.g., antibodies, peptide or polypeptide agents, small molecule compounds, nucleotide agents such as apatmers. In some preferred embodiments, the targeting agent is an antibody or antigen binding fragment (e.g., a Fab fragment). These include various known antibodies that target immune cell surface markers as exemplified herein. They also include antigen-binding fragments (or antibody fragment) that can be readily derived from the known antibodies.

Examples of antibody fragments that can be used as targeting agents of the invention include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an intact antibody; (v) disulfide stabilized Fvs (dsFvs) which have an interchain disulfide bond engineered between structurally conserved framework regions; (vi) a single domain antibody (dAb) which consists of a $V_H$ or $V_L$ domain (see, e.g., Ward et al., Nature 341:544-546, 1989); and (vii) an isolated complementarity determining region (CDR) as a linear or cyclic peptide.

Suitable targeting agents also encompass single chain antibodies. The term "single chain antibody" refers to a polypeptide comprising a $V_H$ domain and a $V_L$ domain in polypeptide linkage, generally linked via a spacer peptide, and which may comprise additional domains or amino acid sequences at the amino- and/or carboxyl-termini. For example, a single-chain antibody may comprise a tether segment for linking to the encoding polynucleotide. As an example, a single chain variable region fragment (scFv) is a single-chain antibody. Compared to the $V_L$ and $V_H$ domains of the Fv fragment which are coded for by separate genes, a scFv has the two domains joined (e.g., via recombinant methods) by a synthetic linker. This enables them to be made as a single protein chain in which the $V_L$ and $V_H$ regions pair to form monovalent molecules.

The various antibodies, antibody-based binding proteins, and antibody fragments thereof described herein can be produced by enzymatic or chemical modification of the intact antibodies, or synthesized de novo using recombinant DNA methodologies, or identified using phage display libraries. Methods for generating these antibodies, antibody-based binding proteins, and antibody fragments thereof are all well known in the art. For example, single chain antibodies can be identified using phage display libraries or ribosome display libraries, gene shuffled libraries (see, e.g., McCafferty et al., Nature 348:552-554, 1990; and U.S. Pat. No. 4,946,778). In particular, scFv antibodies can be obtained using methods described in, e.g., Bird et al., Science 242:423-426, 1988; and Huston et al., Proc. Natl. Acad. Sci. USA 85:5879-5883, 1988. Fv antibody fragments can be generated as described in Skerra and Pluckthun, Science 240:1038-41, 1988. Disulfide-stabilized Fv fragments (dsFvs) can be made using methods described in, e.g., Reiter et al., Int. J. Cancer 67:113-23, 1996. Similarly, single domain antibodies (dAbs) can be produced by a variety of methods described in, e.g., Ward et al., Nature 341:544-546, 1989; and Cai and Garen, Proc. Natl. Acad. Sci. USA 93:6280-85, 1996. Camelid single domain antibodies can be produced using methods well known in the art, e.g., Dumoulin et al., Nat. Struct. Biol. 11:500-515, 2002; Ghahroudi et al., FEBS Letters 414:521-526, 1997; and Bond et al., J. Mol. Biol. 332:643-55, 2003. Other types of antigen-binding fragments (e.g., Fab, $F(ab')_2$ or Fd fragments) can also be readily produced with routinely practiced immunology methods. See, e.g., Harlow & Lane, Using Antibodies, A Laboratory Manual, Cold Spring Harbor Laboratory Press, Cold Spring Harbor, New York, 1998.

In various embodiments, the employed antibody targeting agent can be a chimeric antibody, a humanized antibody or a fully human antibody. When humanized antibodies are used, the antibody should preferably be one with higher homology at amino acid level of the humanized antibody $V_H$ or $V_L$ domains to human antibody $V_H$ or $V_L$ domains than rodent $V_H$ or $V_L$ domains, preferably with a T20 score of greater than 80 as defined by Gao et al. (2013) BMC Biotechnol. 13, pp. 55.

Some sialidase-containing drug conjugates of the invention are intended to target T cells. As noted above, the cell surface marker to be targeted is preferably primarily expressed by normal T cells. In some embodiments, the T cell surface molecule or antigen that is specifically recognized by the targeting agent is not activatory for T cell activation and function, e.g., CD7, CD39, and CD52. In some embodiments, the T cell surface marker that is specifically recognized by the targeting agent is an inhibitory co-receptor (aka checkpoint inhibitor) noted above, e.g., PD1 or CTLA-4. In these embodiments, the employed targeting agent specifically binds to the co-receptor but should not agonize the T cell inhibitory co-receptor. In some preferred embodiments, the targeting agent is an antagonist of the co-receptor, e.g., a blocking antibody or an antigen binding fragment (antibody fragment) thereof. In some embodiments, the targeting agent is a PD1 antagonist antibody or antigen binding fragment thereof. In some embodiments, the targeting agent is a CTLA-4 antagonist antibody or antigen binding fragment thereof. In addition to known antibodies that target CTLA-4 or PD1, the targeting agent in the sialidase-containing conjugates of the invention can also be an antibody that target other inhibitory co-receptors expressed on T cells, e.g., Tim-3, TIGIT and LAG-3.

Any known antagonists of checkpoint inhibitors can be readily employed in the practice of the invention. For examples, many antibodies that target the various T cell surface markers are known in the art. These include antibodies targeting CD5, CD7, CD30, CD39, and CD52. See, e.g., Carriere et al., Exp. Cell Res. 182: 114-28, 1989; Gorczyca et al., Cytometry 50: 177-190, 2002; Weisberger et al., Am. J. Clin. Pathol. 120: 49-55, 2003; Foyil et al., Curr. Hematol. Malig. Rep. 5: 140-7, 2010; Mayer et al., Theranostics. 8(21): 6070-6087, 2018; Perrot et al., Cell Reports 27: 2411-2425, 2019; and Azevedo et al., The Lancet. Neurol. 18: 329-331, 2019. Also known are several antibody drugs targeting checkpoint inhibitors that have been approved by the FDA for treating various types of cancers. These include antibody drugs that target PD-1, Pembrolizumab (Keytruda), Nivolumab (Opdivo) and Cemiplimab (Libtayo), as well as antibody drugs that target CTLA-4, Ipilimumab and Tremelimumab. Some specific sialidase conjugates containing PD1-targeting antibodies are exemplified herein (see, e.g., Examples 7-9). Additionally, a number of other known antibodies targeting checkpoint inhibitors have also been extensively characterized and evaluated for clinical utility. These include, e.g., PD1 antibodies Spartalizumab (PDR001), Camrelizumab (SHR1210), Sintilimab (IBI308), Tislelizuimab (BGB-A317), Toripalimab (JS 001), Dostarlimab (TSR-042, WBP-285), AMP-224 and AMP-514 (MEDI0680). Other than these PD1 and CTLA-4 antibodies, some specific antibodies that block T cell inhibitory co-receptors Tim-3, TIGIT and LAG-3 are also known in the art. See, e.g., Sakuishi et al., J. Exp. Med. 207: 2187-2194, 2010; Rangachari et al., Nat. Med. 18: 1394-1400, 2012; He et al., Onco. Targets Ther. 11:7005-7009, 2018; Hung et al., Oncoimmunology 7: e1466769, 2018; Solomon et al., Cancer Immunol. Immunother. 67: 1659-67, 2018; Wu et al., Cancer Immunol. Res. &: 1700-13, 2019; Grosso et al., J. Clin. Invest. 117: 3383-92, 2007; Wierz et al., Blood 131: 1617-21, 2018; and Nguyen et al., Nat. Rev. Immunol. 15: 45-56, 2015. Any of these known antibodies or antigen binding fragments derived therefrom can be used in constructing the antibody/enzyme conjugates of the invention.

In addition to antibodies, the targeting agent/enzyme conjugates of the invention may also utilize other types of targeting agents that specifically bind to a T cell surface molecule. In some of these embodiments, the targeting agent can be a peptide or mimetic or a small molecule compound that specifically recognizes and binds to the T cell surface molecule. In some embodiments, the T cell surface molecule to be targeted is a checkpoint inhibitor such as PD1 or CTLA-4. Any peptide or small molecule antagonists known in the art may be employed in these embodiments of the invention. For example, there are a number of known small molecule compounds that target PD1/PD-L1 interaction. These include, e.g., compounds AUNP-12, DPPA-1, TPP-1, BMS-202 and CA-170. See, e.g., Li et al., Cancer Immunol. Res. 6: 178-88, 2018; and Wu et al., Acta. Pharmacol. Sin.0: 1-9, 2020. Many other non-antibody agents that target the checkpoint inhibitors are also known in the art. See, e.g., Kopalli et al., Recent Patents on Anti-Cancer Drug Discovery 14: 100, 2019; Guzik et al., Molecules. 24: 2071, 2019; and Lin et al., Eur. J. Med. Chem. 186: 111876, 2020.

V. Conjugating Sialidase to T Cell Targeting Agent

The drug conjugates of the invention contain an immune cell targeting agent described above that is conjugated to a sialidase. Depending on the specific targeting agent used in the conjugates, various means known in the art can be used for linking the enzyme to the targeting agent. See, e.g., Boutureira, O. & Bernardes, G. J. Chem Rev 115, 2174-2195, 2015; Zhang, Y. et al. Chem Soc Rev 47, 9106-9136, 2018; Huang, C. Curr Opin Biotechnol 20, 692-699, 2009; Czajkowsky, D. M. et al. EMBO Mol Med 4, 1015-1028, 2012; Muller, D. BioDrugs 28, 123-131, 2014; Schmidt, S. R. Fusion Protein Technologies for Biopharmaceuticals: Applications and Challenges, 2013; Dai, X. et al. RSC Advances 9, 4700-4721, 2019. In some embodiments, the enzyme can be conjugated to the targeting agent via a chemical linkage routinely used in the art. See, e.g., Boutureira, O. & Bernardes, G. J. Chem Rev 115, 2174-2195, 2015; Zhang, Y. et al. Chem Soc Rev 47, 9106-9136, 2018. In some embodiments, the enzyme can be fused to the targeting agent (e.g., an antibody) via recombinant means in accordance with methods well known in the art. See, e.g., Boutureira, O. & Bernardes, G. J. Chem Rev 115, 2174-2195, 2015; Zhang, Y. et al. Chem Soc Rev 47, 9106-9136, 2018; Huang, C. Curr Opin Biotechnol 20, 692-699, 2009; Czajkowsky, D. M. et al. EMBO Mol Med 4, 1015-1028, 2012; Muller, D. BioDrugs 28, 123-131, 2014; Schmidt, S. R. Fusion Protein Technologies for Biopharmaceuticals: Applications and Challenges, 2013; Dai, X. et al. RSC Advances 9, 4700-4721, 2019.

In some preferred embodiments when the targeting agent is an antibody or antigen binding fragment, the enzyme is typically conjugated to the antibody at sites that do not interfere with antigen binding. For example, conjugation of the targeting antibody to the enzyme should not inhibit the ability of the antibody to form the types of intramolecular and intermolecular associations and bonds that it would otherwise form when non-conjugated. In particular, the site of conjugation on the antibody should not be within the antigen-binding site. Thus, in some preferred embodiments, the sialidase can be conjugated to a targeting antibody (e.g., a full antibody) in the Fc region. In some embodiments, the sialidase can be conjugated to a targeting antibody (e.g., an Fab) in a constant region of the light chain or heavy chain of the antibody.

When the targeting moiety is an antibody, the target cell surface-editing enzyme may be conjugated to any suitable region of the antibody. In certain aspects, the targeting moiety is an antibody having a light chain polypeptide, and the target cell surface-editing enzyme is conjugated to the light chain, e.g., at the C-terminus or an internal region of the light chain. According to certain embodiments, the targeting moiety is an antibody having a heavy chain polypeptide, and the target cell surface-editing enzyme is conjugated to the heavy chain, e.g., at the C-terminus or an internal region of the heavy chain. As exemplifications, conjugates containing sialidase conjugated at the C-terminus or internal region of a PD1-targeting antibody are disclosed herein (see, e.g., Examples 7-9). If the antibody having a heavy chain includes a fragment crystallizable (Fc) region, the target cell surface editing enzyme may be conjugated to the Fc region, e.g., at the C-terminus or an internal region of the Fc region.

As exemplification, to target sialidase to exhausted (PD-$1^+$) T cells, an anti-PD-1 antibody can be chemically conjugated to a recombinant sialidase from mammalian (e.g., Neu1/Neu3) or bacterial (e.g., *S. Typhimurium*) sources. Antibody-sialidase conjugates targeting $HER2^+$ tumors are known in the art, which retain both enzymatic activity and epitope specificity. See, e.g., Xiao et al., Proc Natl Acad Sci USA 113, 10304-9, 2016. These reagents have been used to selectively remove sialic acid ligands of inhibitory Siglecs on the surface of tumor cells. In some embodiments, the conjugation can utilize robust thiol-maleimide and transcyclooctene(TCO)/tetrazine(TZ) chemistries. These biorthogonal reactions allow for selective covalent bond formation in buffered aqueous solutions. As exemplified herein for conjugating anti-PD1 antibodies to a sialidase (Example 7), this enables non-selective coupling of the enzyme to lysine side-chains of the antibody. To enable this conjugation strategy, neuraminidases can be engineered to display a reactive N- or C-terminal cysteine residue. These residues can then be elaborated with maleimide-PEG-TCO (or TZ). Simply combining the antibody-linker-TZ and neuraminidase-linker-TCO conjugates will ligate the two proteins together with 1:1 stoichiometry (Example 7). In some embodiments, a reactive C-terminal cysteine residue for maleimide-PEG-TCO ligation can be engineered onto the antibody, while NHS-TZ can be ligated to lysine side-chains of the neuraminidase. In some embodiments, TCO and TZ groups can be, respectively, ligated to lysine side-chains on either/both antibody or neuraminidase. In some other embodiments, adjusting the molar ratio of the components in the coupling reactions can lead to conjugation of 1, 2, or more sialidase molecules to an antibody molecule, as exemplified herein for anti-PD1 antibodies (Example 7).

Other than non-specific amino acid side chain coupling noted above, conjugation of the targeting moiety (e.g., a T-cell targeting antibody) to the sialidase enzyme can be accomplished via a site-specific linkage. Any methods for site-specific protein conjugation can be used and adapted in the practice of the invention See, e.g., Boutureira, 0. & Bernardes, G. J. Chem Rev 115, 2174-2195, 2015; Zhang, Y. et al. Chem Soc Rev 47, 9106-9136, 2018; Dai, X. et al. RSC Advances 9, 4700-4721, 2019). For example, site-specific conjugation of a sialidase to a PD1 antibody can be performed with sortase-enzyme mediated antibody conjugation ("SMAC"). This SMAC technology was described in detail in WO2014140317. Such a site-specific conjugation strategy is also exemplified herein with PD1 antibody Keytruda (Example 8). Essentially, the PD1 antibody to be conjugated is expressed with a specific C-terminal peptide linker LPXTG (SEQ ID NO:24). The peptide linker serves as a recognition site for the sortase enzyme A from *Staphylococcus aureus* (SrtA). When a glycine modified sialidase is incubated with the antibody and sortase A enzyme, the sortase A enzyme catalyzes a transpeptidation reaction by which the glycine-modified sialidase replaces the C-terminal glycine peptide linker and is covalently coupled to the threonine of the remaining linker sequence, LPXT (SEQ ID NO:25).

VI. Therapeutic Applications

The sialidase-containing conjugates of the invention can promote stimulation and expansion of a population of antigen specific T cells in therapeutic situations where it is desirable to up-regulate an immune response (e.g. induce a response or enhance an existing response). The invention accordingly provides methods for enhancing T cell activation and/or expansion by targeted sialylation on immune cells such as T cells and APCs. In a related aspect, the invention provides methods for stimulating a T cell immune response in a subject by targeted sialylation on immune cells such as T cells and APCs. Typically, these methods are directed to normal T cells, e.g., nonactivated native T cells or activated but non-tumorous T cells. In various embodiments, therapeutic methods of the invention involve contacting a population of T cells (e.g., native or unstimulated T cells) with a sialidase-containing conjugate described herein. Either $CD4^+$ or $CD8^+$ T cells are suitable for methods of the invention. As described herein, some therapeutic methods of the invention are directed to activation of native T cells. In some embodiments, the methods are intended for stimulation of T cells that have formed the immunological synapse with APCs that present a specific antigen. Some other methods of the invention are directed to activating or reviving exhausted T cells as a result of chronic viral infections or cancer.

Subjects suitable for the methods of the invention include human and non-human animals. The therapeutic methods of the invention can be practiced either in vivo, ex vivo, or in vitro. For in vivo applications, the sialidase-containing conjugates of the invention can be directly administered to a subject in need of enhanced T cell activation or stimulation of a T cell immune response. For ex vivo applications, a population of nonactivated T cells or exhausted T cells are first isolated from a subject or a suitable donor. The isolated cells are then stimulated and activated in vitro by culturing with a sialidase-containing conjugate of the invention and optionally, also an immunogenic stimulus agent (e.g., antigen-presenting cells or a non-antigen specific factor (e.g., cytokines)) described herein. The T cell population thus activated can then be introduced into the same or a different subject.

To stimulate an antigen-specific T cell activation or T cell immune response, the sialidase-containing conjugate can be used together with a specific immunogenic stimulus to stimulate an antigen-specific T cell response. As detailed below, this can be administration to a subject in vivo via a combination of the sialidase-containing conjugate and an immunogenic stimulus agent. For in vitro or ex vivo applications, this involves co-culturing the T cells with the sialidase-containing conjugate and an immunogenic stimulus agent. The immunogenic stimulus agent delivers an antigen specific stimulus to the T cells via the antigen-specific T cell receptor (TCR) expressed on the surface of the T cells. In some embodiments, the immunogenic stimulus agent is an antigen for which the TCR is specific. While such antigens will generally be protein, they can also be carbohydrates, lipids, nucleic acids or hybrid molecules having components of two or more of these molecule types, e.g., glycoproteins or lipoproteins. In some embodiments, the immunogenic stimulus can also be provided by other agonistic TCR ligands such as antibodies specific for TCR components (e.g., TCR$\alpha$ chain or TCR$\beta$ chain variable regions) or antibodies specific for the TCR-associated CD3 complex. The immunogenic stimulus antigen include alloantigens (e.g., a MHC alloantigen) on an antigen presenting cell (APC) (e.g., a dendritic cell (DC), a macrophage, a monocyte, or a B cell). Methods of isolating APCs from tissues such as blood, bone marrow, spleen, or lymph node are known in the art, as are methods of generating them in vitro from precursor cells in such tissues.

Also useful as immunogenic stimuli are polypeptide antigens and peptide-epitopes derived therefrom. Unprocessed polypeptides are processed by APC into peptide-epitopes that are presented to responsive T cells in the form of molecular complexes with MHC molecules on the surface of the APC. Useful immunogenic stimuli also include a source of antigen such as a lysate of either tumor cells or cells infected with an infectious microorganism of interest. APC pre-exposed (e.g., by coculturing) to antigenic polypeptides, peptide-epitopes of such polypeptides or lysates of tumor (or infected cells) can also be used as immunogenic stimuli. Such APC can also be "primed" with antigen by culture with a cancer cell or infected cell of interest; the cancer or infected cells can optionally be irradiated or heated (e.g., boiled) prior to the priming culture. In addition, APC (especially DC) can be "primed" with either total RNA, mRNA, or isolated TAA-encoding RNA.

Alternatively, antigen as an immunogenic stimulus be provided in the form of cells (e.g., tumor cells or infected cells producing the antigen of interest). In addition, immunogenic stimuli can be provided in the form of cell hybrids formed by fusing APC (e.g., DC) with tumor cells or infected cells of interest. Methods of fusing cells (e.g., by polyethylene glycol, viral fusogenic membrane glycoproteins, or electrofusion) are known in the art. See, e.g., Gong et al., Proc. Natl. Acad. Sci. USA 97:2716-2718, 2000; Gong et al., Nature Medicine 3:558-561, 1997; Gong et al., J. Immunol. 165(3):1705-1711, 2000. In some other embodiments, the immunogenic stimulus agent to be used can be a heat shock protein bound to antigenic peptide-epitopes derived from antigens (e.g., tumor-associated antigens or antigens produced by infectious microorganisms). Such complexes of heat shock protein and antigenic peptide are useful for facilitating or enhancing uptake of antigenic peptides by APC. See, e.g., Srivastava, Nature Immunology 1: 363-366, 2000. In still some other embodiments, the immunogenic molecules can be derived from a wide range of infectious microorganisms.

Some methods of the invention are specifically directed to activating exhausted T cells. T cells play a key role in orchestrating pathogen-specific adaptive immune responses. Following antigenic clearance, a vast majority of the effector T cells die by apoptosis. A small portion of the cells persist and differentiate into memory T cells. Memory T cells are maintained after the effector phase and can rapidly execute their effector functions in response to reinfection/exposure to previously encountered antigens. The rapid effector function arises when the antigen is present transiently during an acute infection. Nonetheless, this programming of memory T cell differentiation is distinctly altered during chronic viral and bacterial infections, and also in chronic diseases such as cancer due to persistent antigenic exposure and/or inflammation. When altered differentiation progresses, the immune response fails, and antigen-specific T cells progress to a state called T-cell exhaustion.

T cell exhaustion has been associated with the clinical outcomes for multiple human diseases. Exhaustion correlates with persistent viraemia in a number of chronic viral infections including human immunodeficiency virus (HIV), hepatitis C and B virus (HCV and HBV). Interestingly, T-cell exhaustion also plays an important role in cancer and autoimmunity, albeit in opposite ways, in that T-cell exhaustion has been correlated with poor immune responses to tumors in patients and with a better prognosis in patients with autoimmune diseases. When T cell exhaustion markers such as CTLA-4 and PD1 are targeted by the conjugates of the invention, it allows recruiting of sialidase to the most inhibited (exhausted) T cells. In this way, exhausted T cells could be revived through not only enhanced CD28-mediated costimulation, but also simultaneous blockade of inhibitory protein receptors. Since exhausted T cells are often tumor resident, they are also the most likely population to have a TCR specific for tumor antigens, thus making them a highly selective population for tumor cell killing. The sialidase-containing conjugates of the invention can be readily used to reactivate or revive exhausted T cells in subjects with chronic infections or cancer.

The therapeutic methods of the invention can be employed in immunotherapies for a great number of diseases or conditions whereas enhanced immune response is desired. By enhancing antigen-specific T cells activation and/or reactivating exhausted T cells, the sialidase-containing conjugates of the invention can substantially improve clinical efficacy of the immunotherapies. Some therapeutic methods of the invention are directed to stimulating a T cell immune response in subjects suffering from a disease or disorder other than a T cell related cancer. T cell related cancers include any types of lymphoma that affect T lymphocytes, e.g., peripheral T-cell lymphoma, anaplastic large cell lymphoma (ALCL), angioimmunoblastic T-cell lymphoma (AITL), cutaneous T-cell lymphoma (CTCL), adult T-cell leukemia/lymphoma (ATLL), and T-lymphoblastic lymphoma.

In some embodiments, the therapeutic methods of the invention are directed to the treatment of infections by a variety of infectious microorganisms. In some embodiments, the subject in need of treatment is suffering from or afflicted with a viral infection. This includes, e.g., infection by human immunodeficiency virus (HIV), hepatitis B virus (HBV), and hepatitis C virus (HCV). Other examples of infections that are amenable to methods of the invention include influenza virus, measles virus, rabies virus, hepatitis A virus, rotaviruses, papilloma virus, respiratory syncytial virus, feline immunodeficiency virus, feline leukemia virus, and simian immunodeficiency virus.

In some other embodiments, the methods are directed to treating infections by pathogens other than viruses, e.g., bacteria mycoplasma, fungi (including yeasts), and parasites. In various embodiments, the methods can be employed for boosting an immune response against infections by such microorganisms that include, without limitation, Mycobacteria tuberculosis, *Salmonella enteriditis, Listeria monocytogenes, M. leprae, Staphylococcus aureus, Escherichia coli, Streptococcus pneumoniae, Borrelia burgdorferi, Actinobacillus pleuropneumoniae, Helicobacter pylori, Neisseria meningitidis, Yersinia enterocolitica, Bordetella pertussis, Porphyromonas gingivalis, mycoplasma, Histoplasma capsulatum, Cryptococcus neoformans, Chlamydia trachomatis, Candida albicans, Plasmodium falciparum, Entamoeba histolytica, Toxoplasma brucei, Toxoplasma gondii*, and *Leishmania major.*

In some other embodiments, the methods can be used to boost immunotherapies for various types of cancer. For example, subjects afflicted with a cancer can be administered with a sialidase-containing conjugate of the invention. In some other embodiments, cancer cells from a subject or antigen derived therefrom can be contacted with T cells from the subject in vitro in the presence of the sialidase-containing conjugate. The resulting tumor-antigen-specific T cells expanded in vitro are then returned to the subject. Examples of cancers that are suitable for the methods of the invention include, but are not limited to, melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, pancreatic cancer, esophageal cancer, brain cancer, lung cancer, ovarian cancer, cervical cancer, multiple myeloma, hepatocellular carcinoma, nasopharyngeal carcinoma, LGL, ALL, AML, CML, CLL, and other neoplasms known in the art.

In some embodiments, the sialidase-containing conjugates of the invention can be used with other therapeutic agents in combination therapies. For example, the sialidase-containing conjugates can be used together with other non-antigen specific immune-stimulatory agent suitable for treating infections or cancer. In some of these embodiments, they can be used together with immune-checkpoint inhibitor antibodies, e.g., those binding to PD1, PDL1, CTLA4, OX40, TIM3, GITR, LAG3 and the like. In some other embodiments, they can be used together with cytokines such as interferon $\alpha$ and IL-2$\alpha$.

VII. Pharmaceutical Compositions

For use in the therapeutic methods described herein, the invention also provides pharmaceutical compositions that contain a sialidase-containing conjugate of the invention and a pharmaceutically acceptable carrier. Pharmaceutical compositions can be prepared from any of the sialidase-containing conjugates described herein, e.g., a sialidase conjugate containing an antibody targeting a T cell surface marker (e.g., CD5) or PD-1. The pharmaceutically acceptable carrier can be any suitable pharmaceutically acceptable carrier. It can be one or more compatible solid or liquid fillers, diluents, other excipients, or encapsulating substances which are suitable for administration into a human or veterinary patient (e.g., a physiologically acceptable carrier or a pharmacologically acceptable carrier). The term "carrier" denotes an organic or inorganic ingredient, natural or synthetic, with which the active ingredient is combined to facilitate the use of the active ingredient, e.g., the administration of the active ingredient to a subject. The pharmaceutically acceptable carrier can be co-mingled with one or more of the active components, e.g., a hybrid molecule, and with each other, when more than one pharmaceutically acceptable carrier is present in the composition, in a manner so as not to substantially impair the desired pharmaceutical efficacy. Pharmaceutically acceptable materials typically are capable of administration to a subject, e.g., a patient, without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

Pharmaceutical compositions of the invention can additionally contain suitable buffering agents, including, for example, acetic acid in a salt, citric acid in a salt, boric acid in a salt, and phosphoric acid in a salt. The compositions can also optionally contain suitable preservatives, such as benzalkonium chloride, chlorobutanol, parabens, and thimerosal. Pharmaceutical compositions of the invention can be presented in unit dosage form and can be prepared by any suitable method, many of which are well known in the art of pharmacy. Such methods include the step of bringing the antibody of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found, e.g., in Remington: *The Science and Practice of Pharmacy*, Mack Publishing Co., 20$^{th}$ ed., 2000.

Preparation of pharmaceutical compositions of the invention and their various routes of administration can be carried out in accordance with methods well known in the art. See, e.g., Remington, supra; and *Sustained and Controlled Release Drug Delivery Systems*, J. R. Robinson, ed., Marcel Dekker, Inc., New York, 1978. The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and triglycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

EXAMPLES

The following examples are offered to illustrate, but not to limit the present invention.

Example 1 Sialidase Treatment Enhances Activation of T Cells

CD28 recognizes sialic acid containing glycan ligands that compete for binding to its cognate protein ligands CD80 and CD86 and dampen co-stimulation of T cell activation. There is evidence that sialic acid containing ligands are recognized by the co-stimulatory receptor CD28 and compete with its productive engagement with its B7 ligands CD80 and CD86 on the APC (FIG. 1). This effectively reduces recruitment of CD28 to the IS and dampens co-stimulation of T cell activation for both $CD4^+$ and $CD8^+$ T cells.

Figure 2:
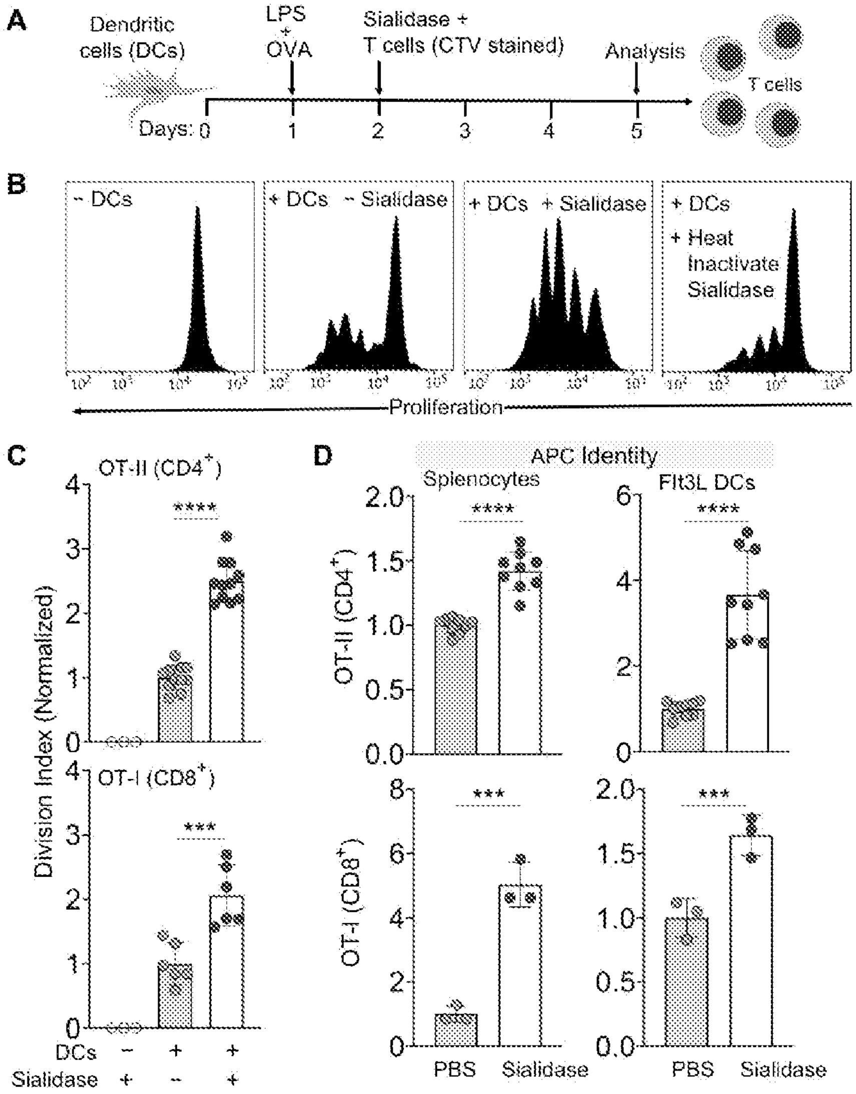
FIG. 2. Sialidase treatment enhances DC activation of T cells. (A) DCs were exposed to chicken ovalbumin and LPS for 24 h at 37° C. After washing, DCs were co-cultured with cell trace violet (CTV)-stained OT-II cells in the presence or absence of sialidase from *V. cholerae* (1:4 DC:T cell ratio). After 3 days, dilution of CTV (a measure of proliferation) was evaluated via flow cytometry. (B) CTV dilution histograms for OT-II cells at day 3 (C) Quantification of T cell activation from (B) and for OT-I cells. Values are plotted as mean±SD (n≥5 biological replicates per condition). (D) Quantification of OT-II and OT-I proliferation induced by different APC systems. Notes: *p≤0.001 and **p≤0.0001, by 1-way ANOVA followed by Tukey's multiple comparisons test.

We observed that enhancement of T cell activation by sialidase is antigen-dependent and APC-dependent. Classic studies on the 'neuraminidase effect' were conducted with presentation of antigen to $CD4^+$ T cells by allogenic APCs. We investigated the applicability of the neuraminidase effect to both $CD4^+$ and $CD8^+$ T cells using transgenic murine T cells sensitive towards the model antigen chicken ovalbumin (OVA) (OT-II=$CD4^+$, OT-I=$CD8^+$ T cells). Here, OT cells were co-cultured with OVA-loaded DCs derived from murine bone marrow precursors and exposed to recombinant sialidase or PBS (FIG. 2A). This experimental setup removes sialic acids from both T cells and the APCs. After 3 days, proliferation of OT cells was assessed via dilution of a proliferative reporter dye (CTV) as measured by flow cytometry (FIG. 2B). Treatment with neuraminidase enhanced both $CD4^+$ and $CD8^+$ T cell proliferation 2-3-fold, with complete dependence on presentation of antigen by the DCs (FIG. 2C). The sialidase enhancement of OT-I and OT-II cell activation was also observed using alternative APC sources including bulk OVA-loaded splenocytes (i.e. mainly B cells) and DCs differentiated using the Flt3L cytokine (FIG. 2D).

Example 2 CD28 Binds Sialylated Glycans

To investigate the molecular mechanisms behind the neuraminidase effect, we recognized that CD28, CTLA-4, PD-1 and all of their B7 ligands have V-set (variable) N-terminal Ig domains that are also found in the sialic acid binding Siglecs, setting up the possibility that one or more of these receptors directly recognize sialic acid ligands. Accordingly, we compared their sequences with all the Siglecs. We found that while they all shared homology with each other, CD28 exhibiting the highest alignment score with Siglecs (FIG. 3).

Figure 4:
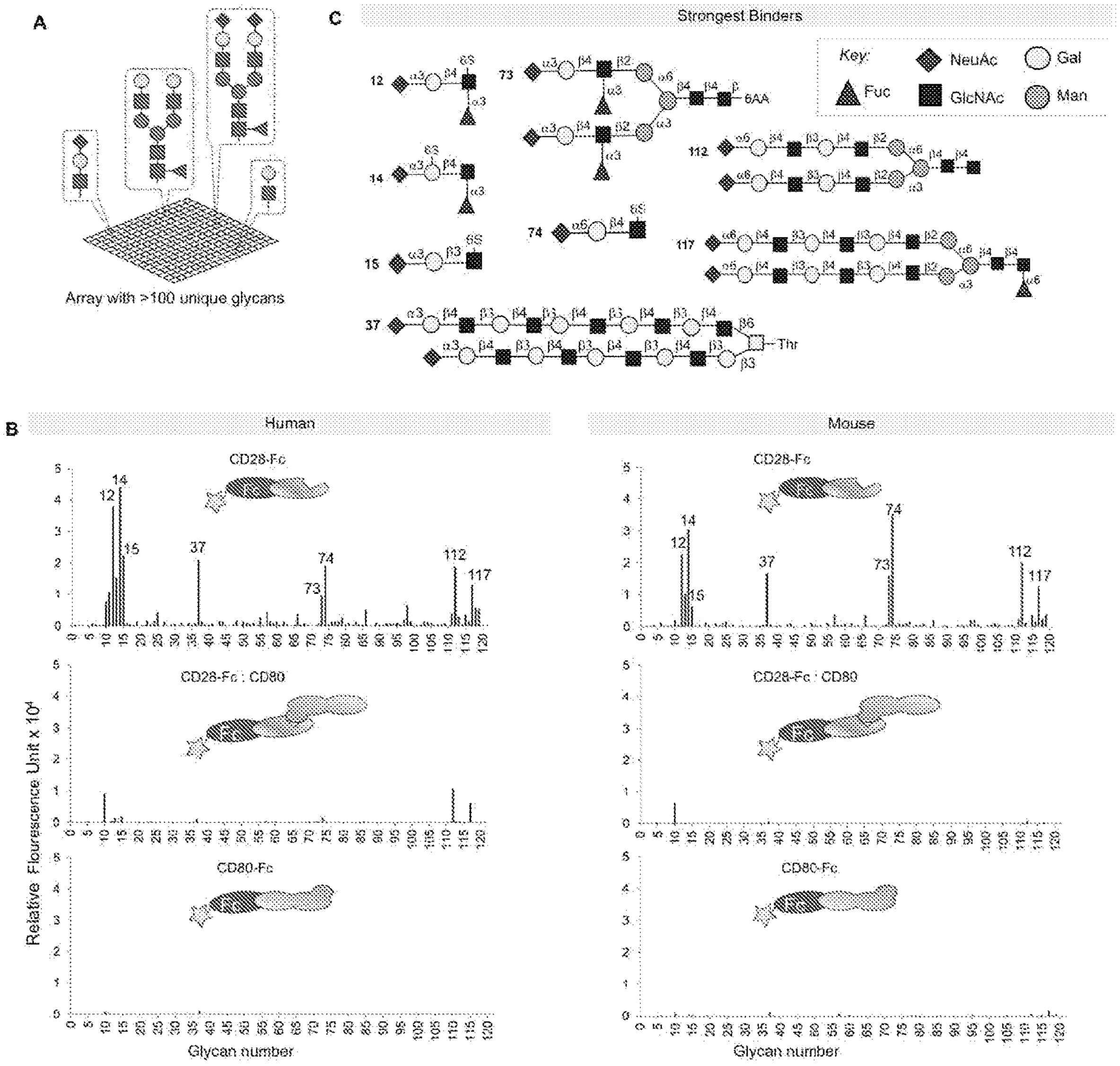
FIG. 4. CD28 binds to sialosides on a glycan array which is blocked by pre-complexing with CD80. (A) Schematic depiction of sialoside glycan microarray. (B) Binding of recombinant CD28-Fc, CD28-Fc-CD80 complex, and CD80-Fc proteins to the glycan microarray. Proteins bound to the array were detected using a fluorescent anti-human Fc (R-phycoerythrin, detected at 532 nm). Plots of fluorescence intensity vs. glycan ID for each protein/protein complex. (C) Structures of strongest binders are presented in symbol notation with their corresponding identification number.

We next tested binding of these proteins on a sialoside glycan microarray we developed to assess the specificity of influenza virus hemagglutinins, Siglecs and other sialic acid specific glycan binding proteins. The array contains a highly diverse library of sialic acid containing glycans (FIG. 4A). This was facilitated by the commercial availability of Fc-chimeras of CD28, CTLA-4, PD-1, CD80, CD86, and PD-L1. Of these, CD28-Fc bound robustly to select sialylated glycans on the array (FIG. 4B). CD28 exhibited preferential binding to extended structures, such as sialylated tri, tetra, and penta LacNAc, but did not display a clear preference for α2,3 or α2,6 linkages to sialic acid (FIG. 4C). Further, we observed significant binding to shorter trisaccharide or sialylated-Lewis X (NeuAcα2-3Galβ1-4(Fucα1-3)GlcNAc) structures, but only when sulfated at the 6 position of the Gal or GlcNAc. No binding was observed to the asialo structures present on the array as controls.

Remarkably, the glycan binding specificity of human and murine CD28-Fc was virtually identical, showing high conservation of sialic acid recognition by CD28 (FIG. 4B). In contrast to CD28-Fc, none of the other Fc-proteins tested bound to the glycan array, as shown here for its cognate receptor, CD80-Fc (B7.1-Fc) (FIG. 4B, bottom). Equally remarkable is when CD28-Fc was precomplexed with CD80, glycan binding of CD28 was largely abolished (FIG. 4B, middle). Similar results were obtained for CD86, and these properties were completely conserved for human and murine proteins. This result suggests that binding of CD80 to CD28 is competitive with binding of sialic acid ligands.

Figure 5:
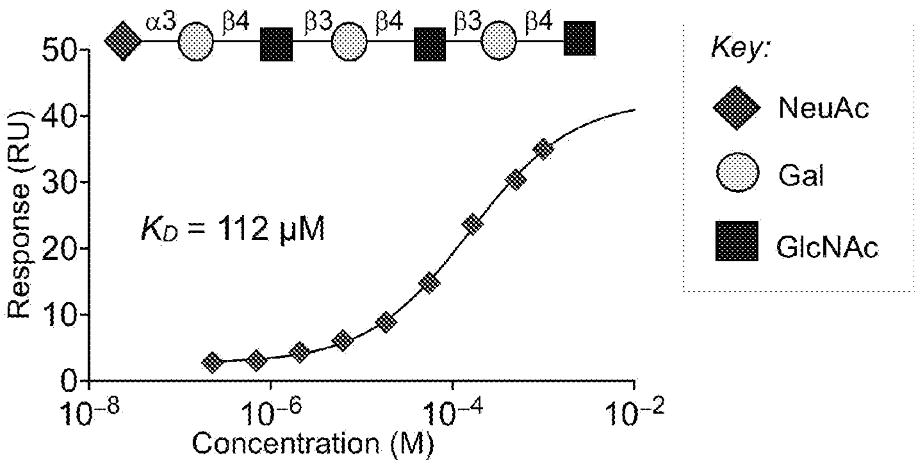
FIG. 5. Biophysical characterization of a CD28-sialoside interaction. Steady state SPR data for α2,3-Sialyl-tri-LacNAc and triLacNAc binding to surface immobilized human CD28.

As an orthogonal test for sialoside binding and to assess the affinity of a sialoside ligand, we tested the ability of surface-immobilized CD28 to bind to a soluble sialylated glycan using SPR. We measured a steady-state $K_d$ of 112 μM (FIG. 5). This compares with the affinity of CD80 for CD28 of 4 μM (van der Merwe et al., J Exp Med 185, 393-403, 1997; and Linsley et al., Immunity 1, 793-801, 1994). So by comparison, the affinity of the sialic acid ligands are relatively weak, but the concentration of sialic acids on the surface of cells is estimated to be very high—25-100 mM—a value that far exceeds the $K_d$ of this soluble glycan for CD28 (Collins et al., Proc Natl Acad Sci USA 101, 6104-9, 2004).

Example 3 Removing Sialic Acid Ligands at IS Increases CD28:CD80 Engagement

Figure 6:
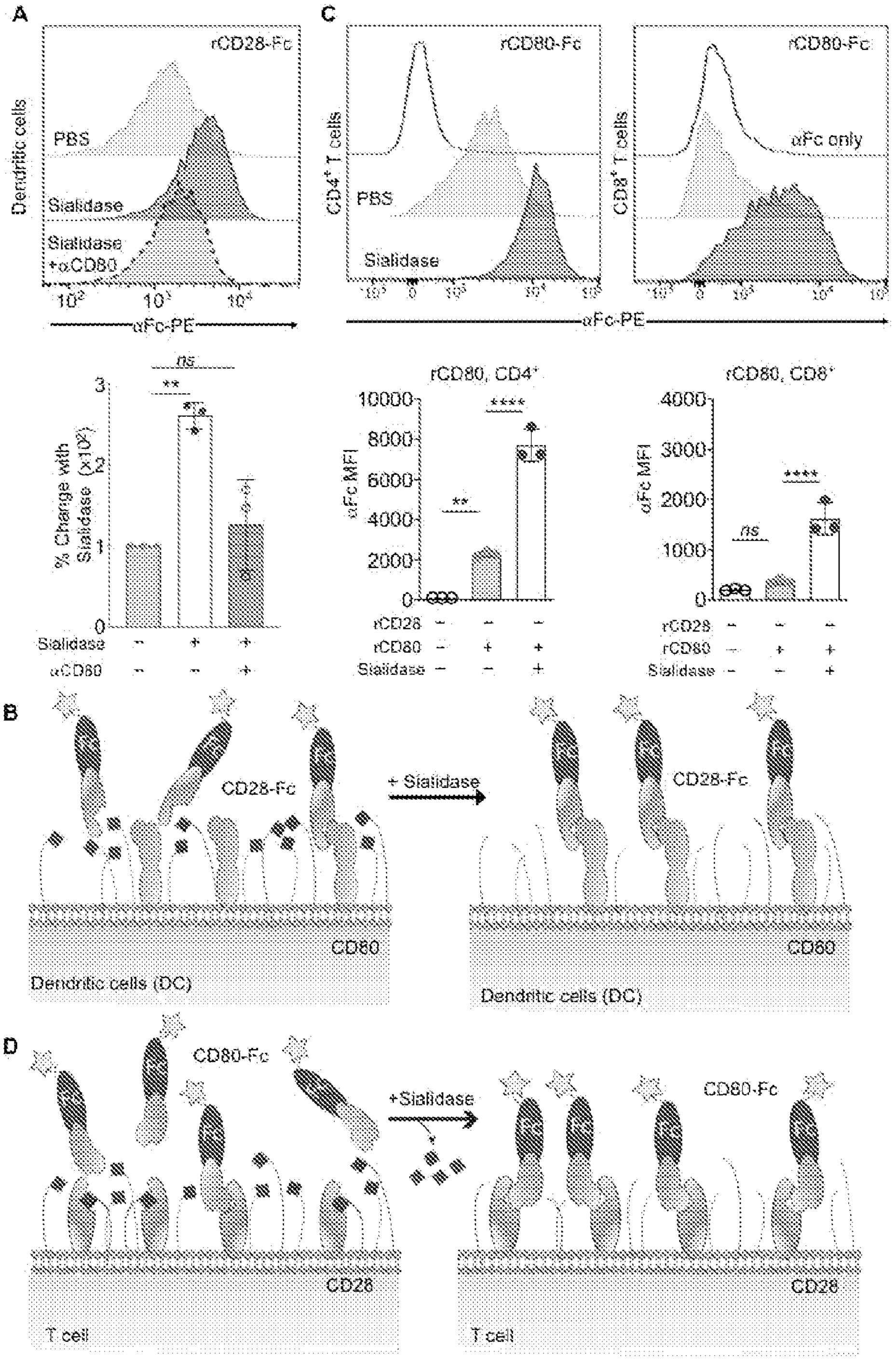
FIG. 6. Desialylation of APC/T cell surfaces enhance binding of recombinant CD28 to CD80. (A) DCs were treated with sialidase (*V. cholerae*) or PBS and subsequently incubated with recombinant chimeric mouse CD28 fused to human Fc (CD28-Fc). Binding was detected with fluorescent anti-human Fc by flow cytometry. Increased binding was blocked with blocking antibody to CD80 (αCD80). (B) Schematic illustrating sialidase removing competing sialic acid ligands for CD28 binding to CD80 on the DC surface. (C) T cells ($CD4^+$ and $CD8^+$) from murine spleen were treated with neuraminidase or PBS and subsequently incubated with recombinant chimeric mouse CD80-Fc. Binding was detected as in (A). (D) Schematic illustrating that sialosides presented in cis on the T cell surface restrict access of CD80 to CD28. Notes: All values are plotted as mean±SD (n=3 biological replicates per condition). p≤0.01, **p≤0.0001, and ns=not statistically significant, by 1-way ANOVA followed by Tukey's multiple comparisons test.

Based on the observation that CD80 in complex with CD28 blocks binding to the sialoside array (FIG. 4B) we reasoned that the reverse may be true in a cellular context, namely that sialic acid ligands compete with binding of CD28 to CD80. To test this, we desialylated DCs (expressing CD80) and T cells (expressing CD28) with sialidase and then mixed each cell type with a fluorescently labeled recombinant construct of their partner co-stimulatory receptor; CD28-Fc for DCs, and CD80-Fc for T cells. In both cases significant enhancement of recombinant protein binding to desialylated cells compared to untreated controls (FIG. 6A,C) was observed, consistent with expectations shown in the illustrations (FIG. 6B,D). These results suggest that sialic acid ligands impede binding of CD80 to CD28 regardless of whether the sialic acid ligands are on the T cell (in cis) or on the APC (in trans) (FIG. 6B,D).

Figure 7:
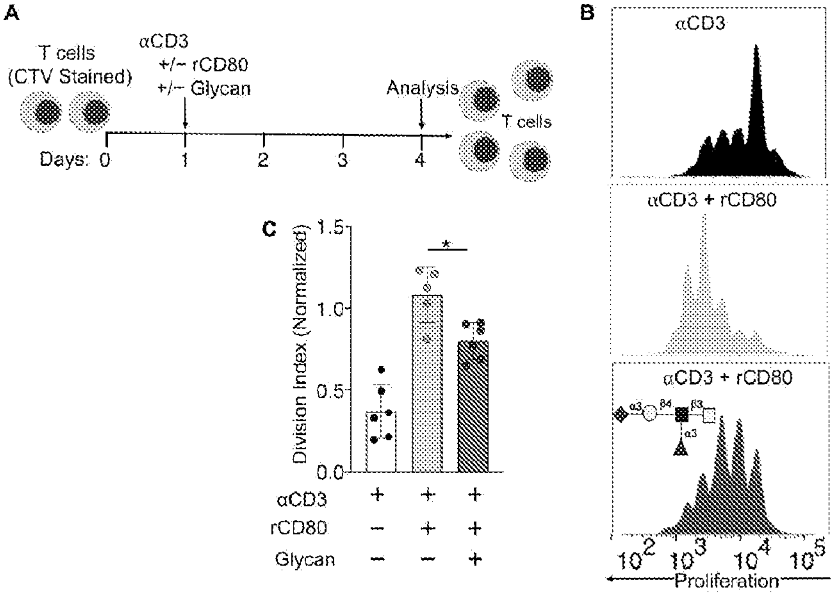
FIG. 7. APC-free expansion of OT-II cells in the presence of soluble glycan (500 μM). (A) Experimental setup. T cells were activated using anti-CD3 (αCD3) and recombinant CD80 (rCD80). (B) OT-II cell proliferation histograms. (C) Quantification of data from (B). Notes: *p≤0.05, by 1-way ANOVA followed by Tukey's multiple comparisons test.

Example 4 Soluble Sialic Acid Ligands Suppress Co-Stimulation of T Cell Activation To provide a functional link between the inhibition of CD80-Fc binding and the impact on CD28 co-stimulation we performed a DC-free T cell expansion assay of $CD4^+$ T cells using anti-CD3 (in place of antigen-loaded MHC) and recombinant CD80-Fc for ligation of CD28 in the presence of a high concentration of sialylated glycan (sialylated-Lewis X) (FIG. 7A), and found that the sialylated ligand caused a significant reduction in T cell proliferation (FIG. 7B,C). Since recombinant CD80 binding to CD28 was the sole source of co-stimulation for T cells in this experiment, we conclude that sialic acid ligands of CD28 functionally suppress CD28 mediated co-stimulation.

Example 5 Sialidase Treated $CD4^+$ T Cells Exhibit Enhanced Proliferation

Figure 8:
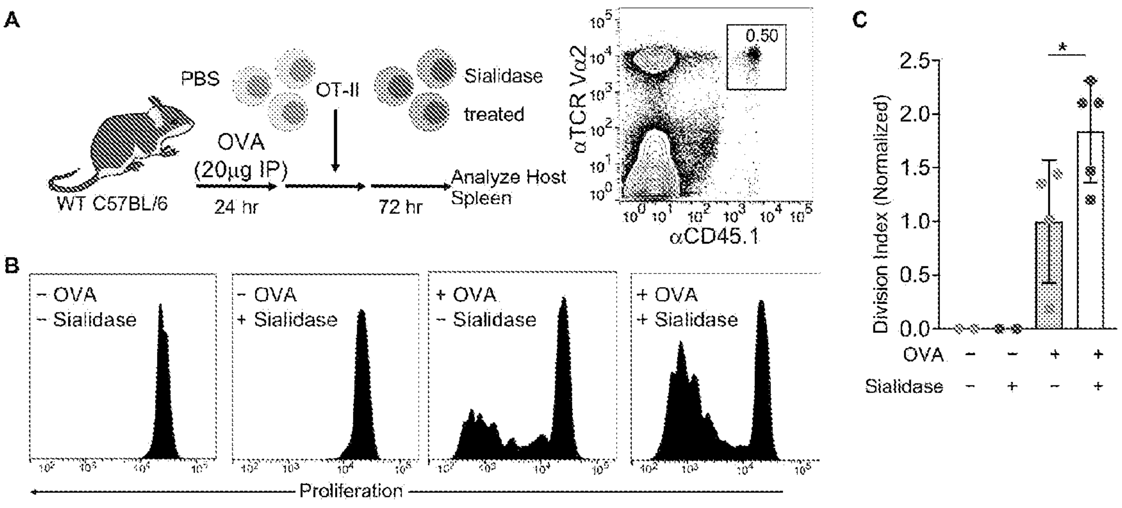
FIG. 8. Desialylated T cells are more readily activated in vivo. (A) WT mice were injected with OVA on day 1. On day 2, OT-II cells were treated with sialidase or PBS ex vivo for 45 min. at 37° C. and subsequently stained with CTV. These cells were then adoptively transferred into OVA experienced host mice (or naïve mice as a control). On day 5, spleens from host mice were analyzed for adoptively transferred OT-II cells and CTV dilution was evaluated. (B) OT-II cells that were desialylated ex vivo exhibit an enhanced ability to proliferate in an antigen-dependent manner in vivo. (C) Quantification of data from (B). Notes: Values are plotted as mean±SD (n≥4 biological replicates per condition). *p<0.05, by 1-way ANOVA followed by Tukey's multiple comparisons test. Normalized division index corresponds to T cell division index for sialidase-treated cultures divided by the division index for the corresponding PBS treated control.

We further observed that sialidase treated $CD4^+$ T cells exhibit enhanced proliferation when adoptively transferred to OVA sensitized mice. To investigate the translatability of these findings to an in vivo system, we adoptively transferred CTV-stained OT-II cells that were desialylated ex vivo into a WT host mouse. We observed that desialylated OT-II cells expanded more efficiently in vivo as compared to a normally sialylated control (FIG. 8). This data suggests that agents that selectively desialylate T cells can be used in vivo to enhance T cell activation in a therapeutic context.

Example 6 Sialidase Enhances Reactivation of Exhausted T Cells

Figure 9:
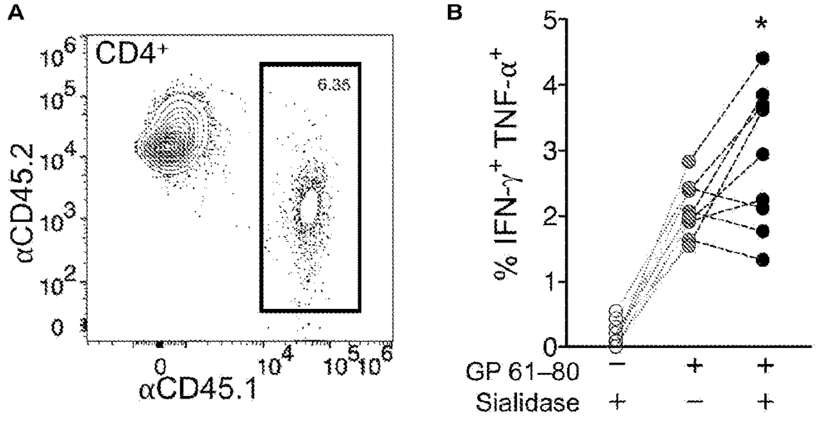
FIG. 9. Desialylation of T cells enhances revival from exhaustion. (A) Delineation of adoptively transferred SMARTA cells ($CD45.1^+$) from WT host ($CD45.2^+$) splenocytes. (B) Intracellular cytokine analysis of exhausted SMARTA cells stimulated with gp13-loaded untreated or sialidase-treated splenocytes from a WT C57BL/6 mouse. Double positive (IFN-$\gamma^+$ TNF-$\alpha^+$) cells are considered revived. Notes: *p<0.05 by 1-way ANOVA followed by Tukey's multiple comparisons test. Paired analysis performed in both biological and technical triplicate.
Figure 10:
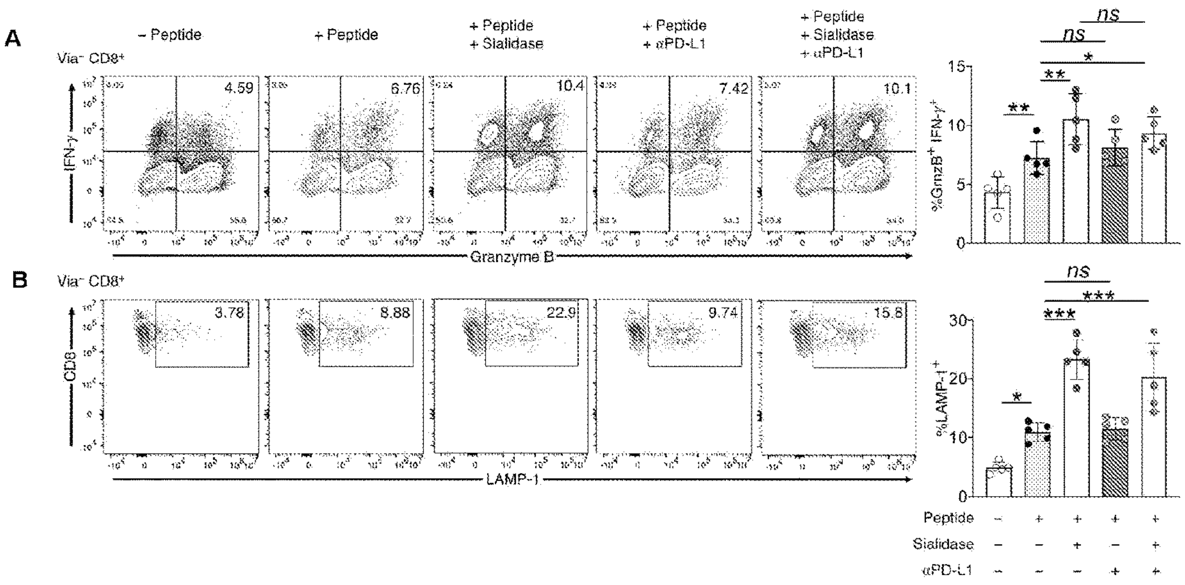
FIG. 10. Sialidase enhances reactivation of T cells exhausted via chronic lymphocytic choriomeningitis virus (LCMV) infection. WT C57BL/6J mice were infected with $2\times10^6$ PFU LCMV (Clone 13) to establish chronic viral infection. After 10 days, spleens were harvested and suspended splenocytes were treated with the immunodominant GP33-43 LCMV-derived peptide antigen for 6 h. (A) Polyclonal $CD8^+$ T cells were reactivated by the peptide as indicated by an increased percentage of cells that expressed the anti-viral cytokine interferon gamma (IFN-γ) and cytotoxic enzyme granzyme B. Addition of sialidase enhanced activation over peptide alone. Treatment with a benchmark anti-checkpoint antibody (anti-PD-L1, 25 μg/mL) did not enhance T cell activation over peptide alone. (B) Expression of lysosomal-associated membrane protein 1 (LAMP-1)—important for release of cytotoxic proteins such as granzyme B—was also enhanced by sialidase over peptide alone. Numbers within gates represent percentage of total cells within the gate. Via=viability dye. *p<0.05, p≤0.01, *p≤0.001, p≤0.0001, by one-way ANOVA followed by paired Dunnett's multiple comparisons test. ns=not significant.

We further examined effect of desialylation on exhausted T cells. Chronic infection with lymphocytic choriomeningitis virus (LCMV) produces exhausted, PD-$1^+$ T cells. This model system is considered a gold standard for studying mechanisms governing T cell exhaustion. We used the LCMV system to assess the ability of sialidase to revive functionally exhausted T cells in an antigen-specific manner in vitro. To produce LCMV-specific exhausted T cells, we adoptively transferred purified LCMV antigen-specific 'P14' $CD8^+$ T cells into WT host mice that will be subsequently infected with LCMV. P14 cells are present in mice that are transgenic for a TCR that recognizes a specific peptide from LCMV (gp33) in the context of MHC I in C57BL/6 mice. After 8-14 days of residency in the infected host mouse, P14 cells become functionally exhausted as they experience overstimulation through the LCMV-specific TCR. See, e.g., Pircher et al., Nature 346: 629-33, 1990; and Barber et al., Nature 439: 682-7, 2006. Exhausted P14 cells can be retrieved from host spleens and used immediately in vitro—delineation of cells can be achieved using a fluorescent antibody against the alternative allele of CD45 (CD45.1/Ly5a) that is not present in WT C57BL/6 mice, but is highly expressed on our transgenic cells. As shown in FIG. 9 and FIG. 10, our studies showed that treatment of T cells exhausted via chronic LCMV infection with sialidase enhances reactivation of the T cells. Specifically, cytokine production (i.e. IFN-γ/TNF-α) was enhanced in exhausted P14 cells following stimulation with antigen (gp33)-loaded APCs from WT C57BL/6 (FIG. 9B). In addition, expression of lysosomal-associated membrane protein 1 (LAMP-1), which is important for release of cytotoxic proteins such as granzyme B, was also enhanced by sialidase treatment (FIG. 10B). These findings are consistent with the expected increase in stimulation through CD28/B7 resulting from reduced trans sialoside ligands of CD28.

Example 7 Sialidase can be Conjugated to a T Cell-Specific Antibody Through Tetrazine-TCO Ligation to Anti-PD-1

Figure 11:
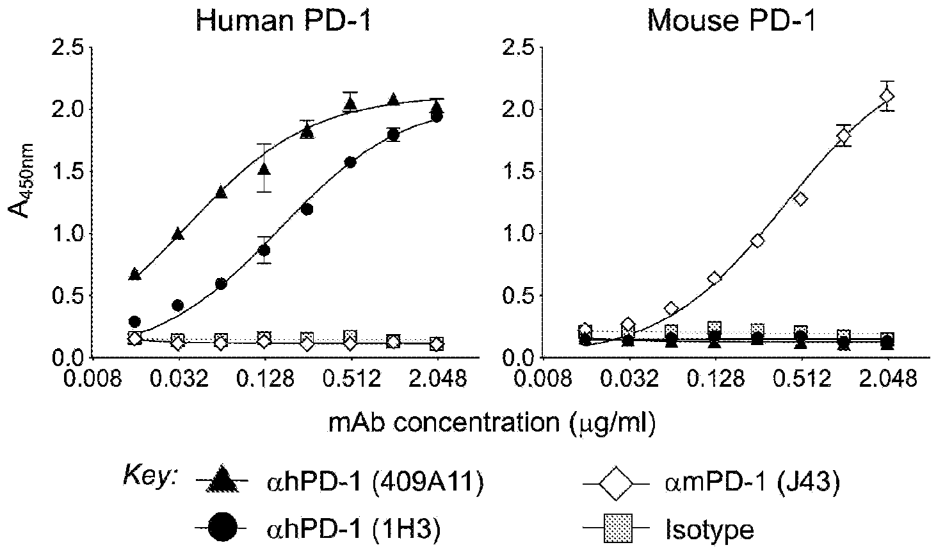
FIG. 11. Three expressed anti PD-1 monoclonal antibodies targeted respectively to either human PD-1 (hPD1) and mouse PD-1 (mPD1) bind with high specificity and affinity. Antibody clones to hPD1 (αhPD1) 1H3 and 409A11 (Keytruda/Pembrolizumab) bind hPD1 with $EC_{50}$ values of 160 ng $mL^{-1}$ and 36 ng $mL^{-1}$, respectively, and no affinity for mPD1. An anti-mPD1 (αmPD1) clone J43 binds mPD1 with $EC_{50}$ of 390 ng $mL^{-1}$, and no affinity for hPD1.
Figure 12:
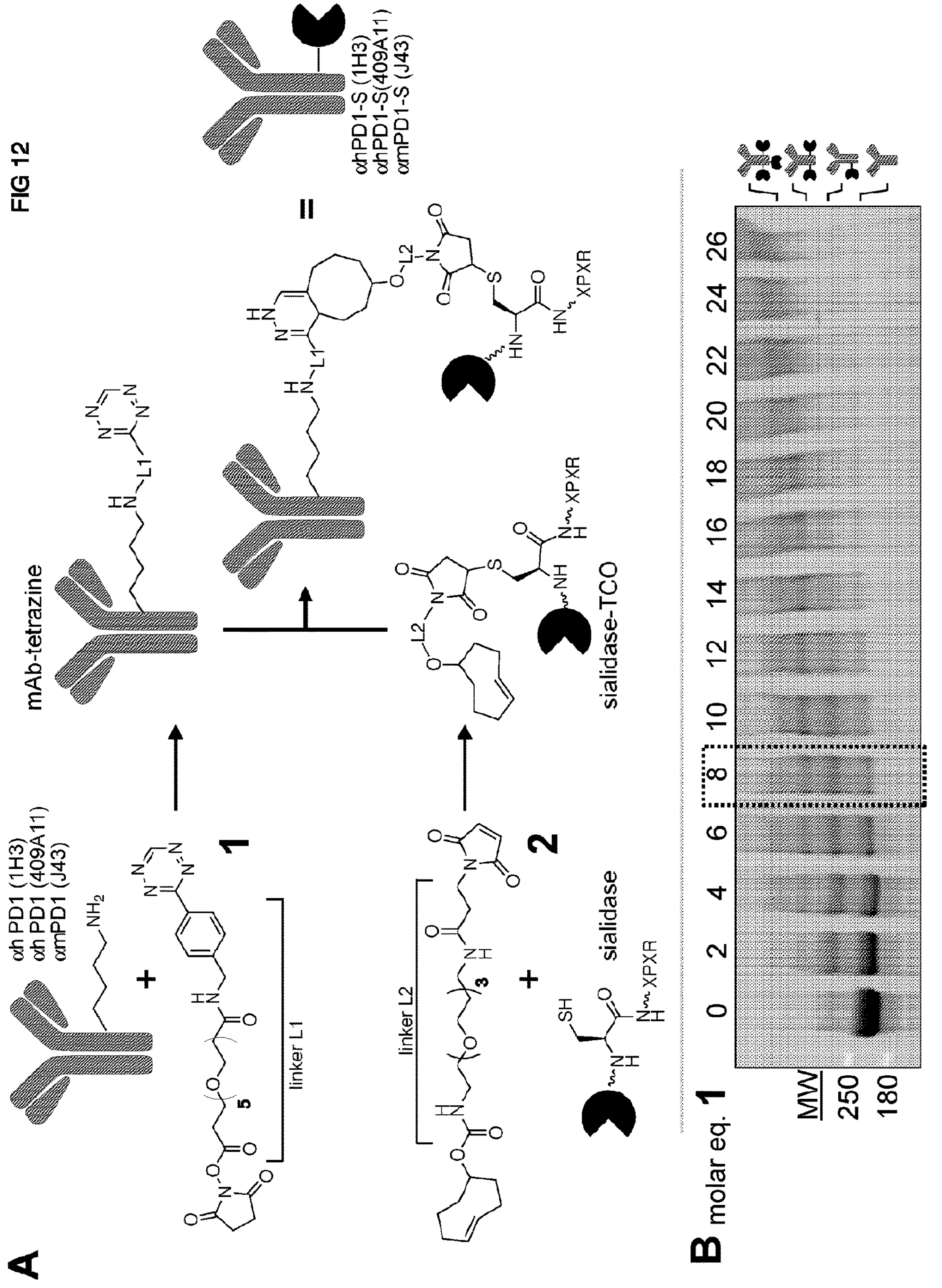
FIG. 12. Production of a sialidase targeted to murine PD-1 via antibody-sialidase tetrazine-TCO conjugation. (A) Cartoon schematic of a non-site-specific ligation of an αPD-1 monoclonal antibody to a specifically modified sialidase. αPD-1 is incubated with NHS-tetrazine 1 (upper portion), non-selectively labeling solvent-exposed lysine residue side-chains. Simultaneously, an expressed sialidase (S), modified with a C-terminal cysteine, is incubated with 40-fold molar excess of TCO-maleimide 2 under slightly reducing conditions (lower portion), leading to selective modification of the free thiol group. Tetrazine-antibody and TCO-sialidase react through inverse Electron Demand Diels Alder (iEDDA) reaction under ambient conditions to afford covalently conjugated αPD1-S. (B) Example conjugation of tetrazine-modified αmPD1 clone J43 to TCO-modified bacterial sialidase from *Salmonella typhimurium* (ST). Lanes represent varying molar ratios of the NHS-tetrazine (1) used to prepare αmPD1 (J43), with all reactions incubated with a 10-fold molar excess of TCO-ST for 1 hour at room temperature to achieve final conjugation. All lanes are shown non-reduced to estimate degree of modification as a function of the number of ST molecules conjugated per antibody. The boxed region at molar ratio of 8 represents an optimum condition selected for large-scale production, where most αmPD1 (J43) starting material has reacted and most product appears to consist of single- or double-ST-modified antibody.
Figure 13:
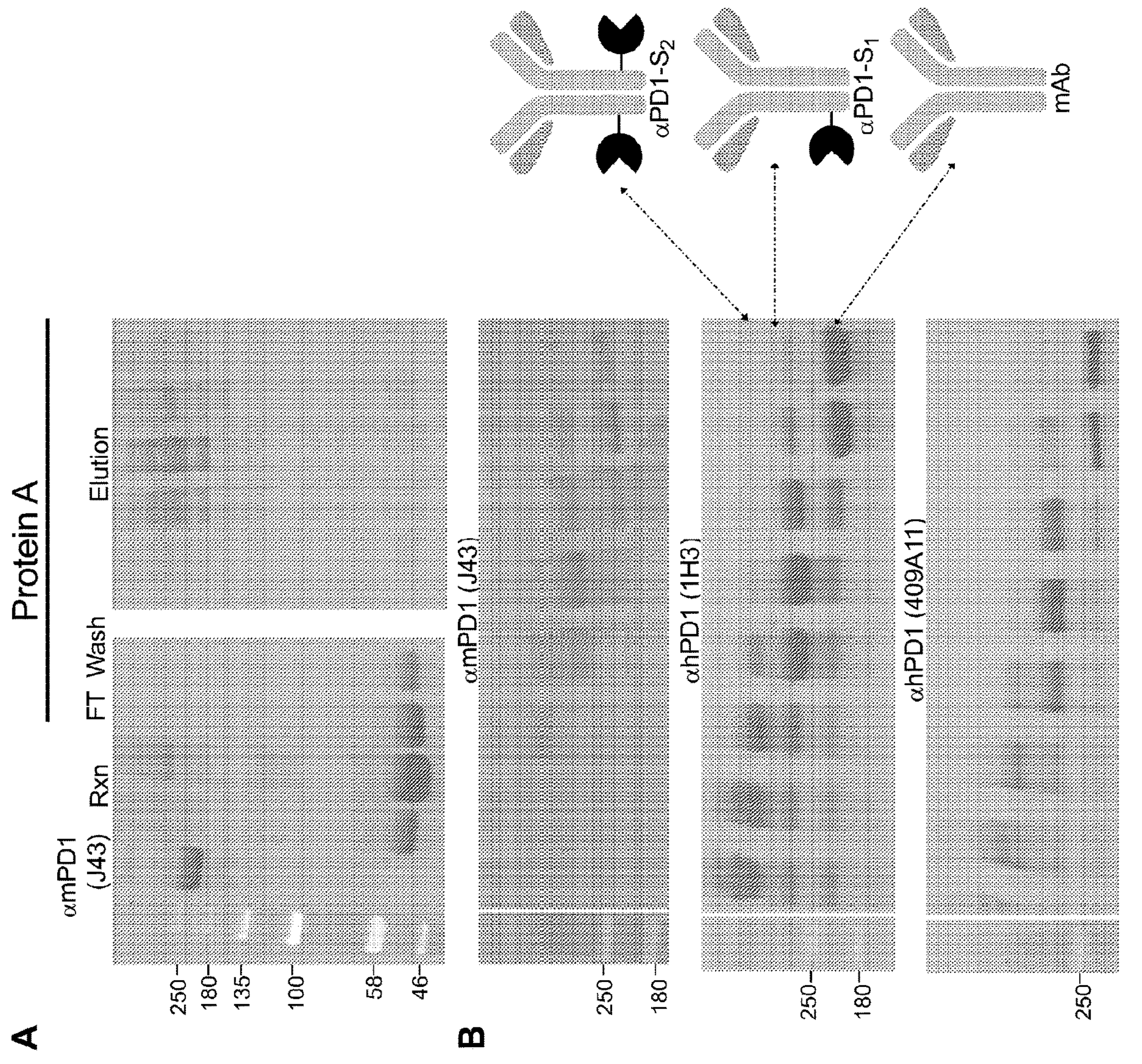
FIG. 13. Large-scale production of αPD1-S via tetrazine-TCO conjugation. Using optimized conditions determined in FIG. 12 αPD1-S conjugates for the three αPD1 clones were prepared at 2-20 mg antibody scale and purified. (A) Example Protein A purification of αmPD1-S (J43) showing antibody starting material, reaction product/column load, flow-through, wash, and elution samples, leading to successful removal of excess free TCO-ST. (B) Final size-exclusion chromatography (SEC) purification of all three αPD1-S clones via a Superdex 200 (S200) column. SEC purification gives successful separation of unmodified antibodies from αPD1-S conjugates.

PD-1 is expressed on exhausted and hypofunctional T cells, particularly on tumor-infiltrating lymphocytes (TTLs), and antagonistic anti-PD-1 antibodies (PD1) capable of blocking interactions with PD-L1 have already been shown to be effective anti-cancer therapeutics through reactivation of exhausted and hypofunctional T cells. We thus demonstrated that sialidases capable of further enhancing T cell reactivation can be targeted to T cells through conjugation to existing anti-PD-1 antibodies. We investigated the possibility of using non-specific small-molecule linkers to install multiple reactive sites on three expressed αPD1 monoclonal antibodies. We expressed and purified three αPD1 monoclonal antibodies: two specific for human PD-1 (hPD1), clones 1H3 and 409A11 (Keytruda/Pembrolizumab); and one with specificity for mouse PD-1 (mPD1), clone J43 (FIG. 11). Through an inverse Electron Demand Diels Alder (iEDDA) reaction, two molecules conjugated respectively with tetrazine and TCO moieties can react rapidly and covalently under ambient conditions. Utilizing the methodology and reagents shown in the reaction scheme in FIG. 12A, we incubated αPD1 antibody clones with NHS-tetrazine 1, allowing non-selective labeling of solvent-exposed lysine residue side-chains (FIG. 12A). Simultaneously, we modified an expressed sialidase from *Salmonella typhimurium* (ST) containing a C-terminal cysteine though incubation with a 40-fold molar excess of TCO-maleimide 2, leading to near-complete selective modification of the free thiol group (FIG. 12A). To optimize conjugation yield, leading to maximum utilization of antibody starting material while also producing defined products with small numbers of ST per antibody, we titrated the molar ratio of NHS-tetrazine used to load the antibody with reactive groups in step one of the conjugation reaction (FIG. 12B). We identified a molar ratio of 8:1 NHS-tetrazine to mAb, followed by a 10-fold molar excess of ST-TCO incubated for one hour at room temperature produced an optimum reaction condition where the vast majority of input αPD1 is modified, but the major products consist of only single- or double-ST-modified αPD1-S species (see highlighted boxed region in FIG. 12B). For scale-up, we utilized all three αPD1 clones, 1H3, 409A11 (Keytruda/Pembrolizumab), and J43 at 2-20 mg antibody scale, reacting under optimized conditions. For purification, we found that αPD1-S pools could easily be separated by either a combination of Protein A and size exclusion chromatography (SEC) or SEC alone, leading to successful removal of both excess unreacted ST-TCO and unmodified mAb species. (FIG. 13). For all clones, final SEC fractions corresponding to single- and double-modified αPD1-S (FIG. 13B) were pooled, concentrated, and characterized for targeted sialidase functionality. We observed by ELISA that the purified J43 construct had equivalent binding to mPD-1 shown in FIG. 11. Purified 1H3, 409A11 (Keytruda/Pembrolizumab), and J43 had 132 U mL-1, 26 U mL-1, and 36 U mL-1, respectively, respectively against MUNANA (1 activity unit=1 μmol min-1).

Example 8 Sialidase can Also be Conjugated to a T Cell-Specific Antibody Through Site-Specific Ligation to Anti-PD-1

Figure 14:
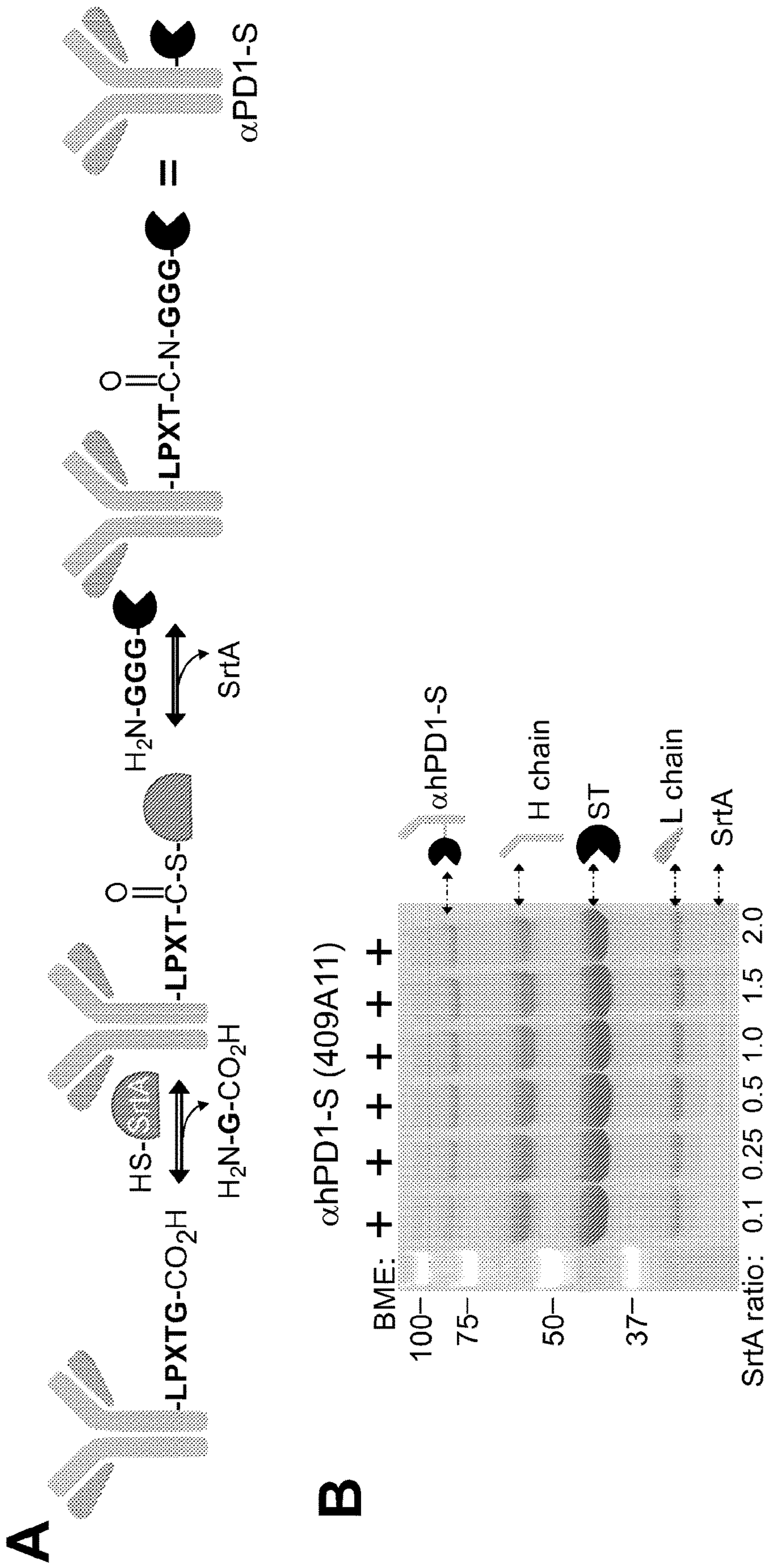
FIG. 14. Site-specific conjugation of a sialidase to an αhPD1-antibody using bacterial sortase. (A) Cartoon schematic of a site-specific ligation of an αPD1 monoclonal antibody to sialidase catalyzed by bacterial sortase (SrtA). The C-terminus of each antibody heavy chain is modified with a specific SrtA recognition peptide (LPXTG; SEQ ID NO:24), forming a transient covalent intermediate containing LPXT (SEQ ID NO:25) with a reactive thiol in the SrtA active site. In the second enzymatic step, an expressed sialidase, modified with an N-terminal poly-glycine motif (GGG), is utilized as a nucleophile within the SrtA active site to release the covalent intermediate, resulting in site-specific joining of an αPD1 to sialidase (S) to form the PD-1-targeted sialidase conjugate, αPD1-S. (B) Example conjugation of αhPD1 clone 409A11 to a bacterial sialidase from *Salmonella typhimurium* (ST) with varying molar ratios of the SrtA catalyst. A six-fold molar excess of ST was added to one equivalent αhPD1 and incubated in the presence of varying molar ratios of SrtA for three hours at room temperature. All lanes are shown under reducing conditions.

To demonstrate broad utility, we showed that αPD1-S conjugates could also be generated by site-specific modification methods. Firstly, we modified the C-terminus of each antibody heavy chain with a specific bacterial sortase (SrtA) recognition peptide (LPXTG; FIG. 14A). Through a reactive thiol present on a cysteine residue within the active site, SrtA forms a transient covalent intermediate with molecules bearing the C-terminal LPXTG peptide motif, which is subsequently released via nucleophilic attack from a second molecule bearing a separate N-terminal GGG peptide recognition motif SrtA thus catalyzes a site-specific ligation of two molecules via formation of a LPXT-GGG peptide bond (FIG. 14A). We used SrtA to assess the possibility of targeting a sialidase enzyme to exhausted T cells through specific conjugation of a GGG-modified sialidase from *Salmonella typhimurium* (ST) to a human PD-1-specific monoclonal antibody, 409A11 (Keytruda/Pembrolizumab), leading to formation of an αhPD1-sialidase fusion molecule (αhPD1-S). As shown in FIG. 14B, when added to a mixture containing a six-fold molar excess of ST and one equivalent αhPD1, varying molar ratios of SrtA lead to formation of an ST-modified αhPD1 heavy chain. Subsequently, we modified the C-terminus of each antibody heavy chain with a "SMARTag" CXPXR motif, which can be oxidized by formylglycine-generating enzyme (FGE) either in vitro or in vivo, to generate formylglycyl-antibodies (fGly-mAb). We condensed the fGly group with 40 molar equivalents of Hydrazino-Pictet Spengler (HIPS)-azide at pH 5.5 to finally produce antibody species modified with a specific C-terminal azide (mAb-N3). In parallel, we generated a mutually reactive ST sialidase-dibenzylcyclooctene (ST-DBCO) by conjugation of a reactive ST cysteine sulfhydryl with 40 molar equivalents of DBCO-maleimide under mildly reducing conditions at pH 8.0. We observed that mAb-N3 species reacted with 20 molar equivalents of ST-DBCO in a strain-promoted azide-alkyne cycloaddition (SPAAC) to afford specifically conjugated αPD1-S reagents.

Figure 15:
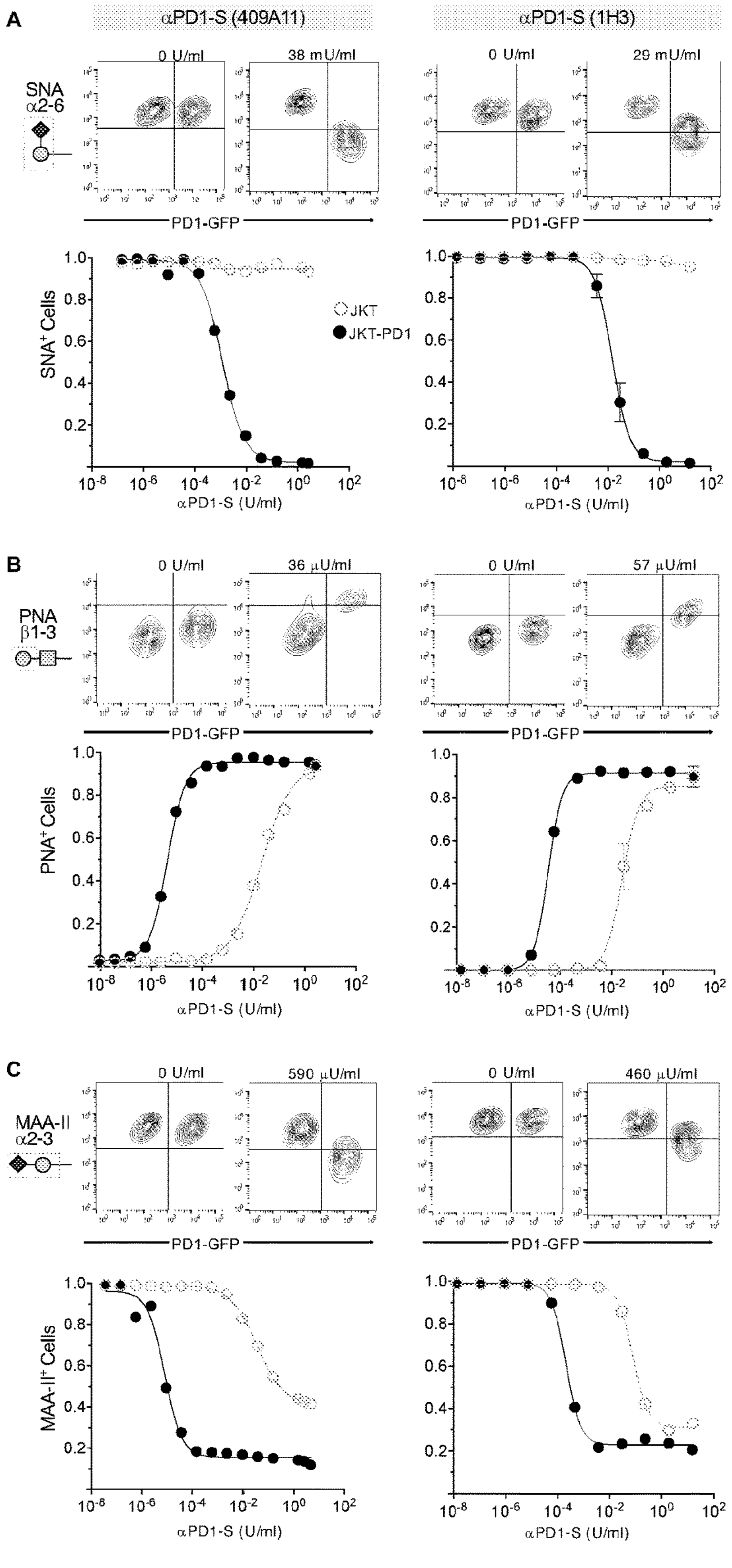
FIG. 15. Sialidase conjugated to anti-PD-1 enhances desilylation of T cells expressing PD-1.

Example 9 PD-1-Targeted Sialidase, αPD1-S, Selectively Enhances Desialylation of PD-1-Expressing T Cells We investigated the impact of targeting sialidase to the surface of T cells by comparing the desialylation of Jurkat T cell lines with and without cell surface expression of PD-1. We used Jurkat cells and Jurkat cells expressing chimeric PD-1 fused to green fluorescent protein (Jurkat-PD1-GFP; Zhao, Y. et al. Cell Rep 24, 379-390 e6, 2018). Since these two cell lines can be readily distinguished by flow cytometry due to expression of GFP in the Jurkat-PD1-GFP cells, it is possible to treat them with αPD1-S as a mixture, and use flow cytometry to determine the degree to which the different T cell populations become desialylated. To assess the degree of desialylation we used three different lectins that recognize the substrates or products of several different sialic acid containing glycans: *Sambucus nigra* agglutinin (SNA) that recognizes sialic acid in the NeuAcα2-6Galβ1-4GlcNAc sequence, commonly found in N-linked glycans on cell surface proteins; peanut agglutinin (PNA) that recognizes Galβ1-3GalNAc, which is the product of desialylation of the sequence NeuAcα2-3Galβ1-3GalNAc commonly found in O-linked glycans of cell surface proteins; and *Maackia amurensis* agglutinin II (MAA-II) that recognizes NeuAcα2-3Gal linkages found in both N-linked and O-linked glycans of cell surface glycoproteins. In FIG. 15, we show efficiency of desialylation of Jurkat-PD1-GFP T cells, relative to Jurkat T cells that do not express PD-1, following incubation with αPD1-S reagents over a range of concentrations from 10 to 1×10-7 U mL-1. The results show enhanced desialylation of the Jurkat-PD1-GFP cells achieving similar levels of desialylation to native Jurkat cells at 100-1000-fold lower levels of αPD1-S regardless of which lectin was used for detection of desialylation (FIG. 15). While the amount of αPD1-S required to achieve desialylation varied for the glycan structures recognized by the three individual lectins, the degree of enhancement was similar for all three, showing the dramatic impact of specific targeting of sialidase to the surface of T cells.

The invention thus has been disclosed broadly and illustrated in reference to representative embodiments described above. It is understood that various modifications can be made to the present invention without departing from the spirit and scope thereof. It is further noted that all publications, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. A targeting agent-enzyme conjugate, comprising (a) an antibody moiety that specifically recognizes programmed cell death protein 1 (PD1), and (b) a sialidase or enzymatically active fragment thereof; wherein the conjugate is capable of enhancing sialidase mediated removal of sialic acids from a cell expressing PD1 by at least 5 fold, relative to a cell not expressing PD1.

2. The conjugate of claim 1, wherein the sialidase is a human sialidase, a bacterial sialidase, or a viral sialidase.

3. The conjugate of claim 2, wherein the human sialidase is human neuraminidase 1 (Neu1), neuraminidase 2 (Neu2), neuraminidase 3 (Neu3), or neuraminidase 4 (Neu4).

4. The conjugate of claim 1, wherein the antibody moiety is fused to the enzyme covalently.

5. The conjugate of claim 1, wherein the antibody moiety is human PD1 antibody clone 409A11 or clone 1H3.

6. The conjugate of claim 1, wherein the sialidase is a *Salmonella typhimurium* sialidase.

7. The conjugate of claim 1, wherein the sialidase is fused non-selectively to lysine side chains of the antibody.

8. The conjugate of claim 1, wherein the sialidase is fused site-specifically to the C-terminus of the antibody.

9. The conjugate of claim 1, which is capable of enhancing sialidase mediated removal of sialic acids from a cell expressing PD1 by at least 100 fold, relative to a cell not expressing PD1.

10. A method for enhancing T cell activation and expansion, comprising contacting a population of non-cancerous T cells with a targeting agent-enzyme conjugate of claim 1, thereby enhancing T cell activation and expansion.

11. The method of claim 10, wherein the population of T cells are contacted with the targeting agent-enzyme conjugate in vivo.

12. The method of claim 10, wherein the population of T cells are contacted with the targeting agent-enzyme conjugate ex vivo.

13. The method of claim 10, wherein the population of T cells are $CD8^+$ T cells or $CD4^+$ T cells.

14. The method of claim 10, wherein the population of T cells are naïve T cells.

15. The method of claim 10, wherein the population of T cells are exhausted T cells.

16. The method of claim 10, wherein the population of T cells are contacted with the conjugate in the presence of a specific antigen.

17. The method of claim 16, wherein the specific antigen is presented by an antigen presenting cell.

18. A method for stimulating a T cell immune response in a subject, comprising administering to the subject a targeting agent-enzyme conjugate of claim 1, thereby stimulating a T cell immune response in a subject.

19. The method of claim 18, wherein the subject is not afflicted with a T cell lymphoma.

20. The method of claim 18, wherein the subject is suffering from a solid tumor or an infection.

* * * * *